(12) United States Patent
Barwell et al.

(10) Patent No.: US 9,222,941 B2
(45) Date of Patent: Dec. 29, 2015

(54) GLUCOSE SENSOR MOLECULES

(75) Inventors: Nicholas Paul Barwell, Coventry (GB); Tony James, Bath (GB)

(73) Assignee: Lightship Medical Limited, London (GB)

( * ) Notice: Subject to any disclaimer, the term of this patent is extended or adjusted under 35 U.S.C. 154(b) by 50 days.

(21) Appl. No.: 13/979,123

(22) PCT Filed: Jan. 10, 2012

(86) PCT No.: PCT/GB2012/000018
§ 371 (c)(1), (2), (4) Date: Jan. 22, 2014

(87) PCT Pub. No.: WO2012/095628
PCT Pub. Date: Jul. 19, 2012

(65) Prior Publication Data
US 2014/0147934 A1    May 29, 2014

Related U.S. Application Data

(60) Provisional application No. 61/431,756, filed on Jan. 11, 2011.

(51) Int. Cl.
*G01N 33/66* (2006.01)
*C07F 5/02* (2006.01)

(52) U.S. Cl.
CPC .............. *G01N 33/66* (2013.01); *C07F 5/025* (2013.01)

(58) Field of Classification Search
CPC ....................................................... C12N 9/00
See application file for complete search history.

(56) References Cited

U.S. PATENT DOCUMENTS

| 6,387,672 | B1 | 5/2002 | Arimori et al. |
| 7,358,094 | B2 * | 4/2008 | Bell et al. ............... 436/172 |
| 8,141,409 | B2 | 3/2012 | Crane et al. |

FOREIGN PATENT DOCUMENTS

| WO | 2010/116142 | 10/2010 |
| WO | 2011/101624 | 8/2011 |

(Continued)

OTHER PUBLICATIONS

Gray et al., "Boronate derivatives of bioactive amines: potential neutral receptors for anionic oligosaccharides," *Tetrahedron Letters*, 2003, 44:3309-3312.

(Continued)

*Primary Examiner* — Shafiqul Haq
*Assistant Examiner* — Nam Nguyen
(74) *Attorney, Agent, or Firm* — Fish & Richardson P.C.

(57) ABSTRACT

The present invention provides a glucose sensor having a glucose receptor containing a binding site of formula (I): wherein X, n, m and $R_1$ are defined herein. Also provided is a glucose sensor molecule for use in such a glucose sensor, the glucose sensor molecule containing the binding site of formula (I). The binding site has been found to have particularly good selectivity for glucose.

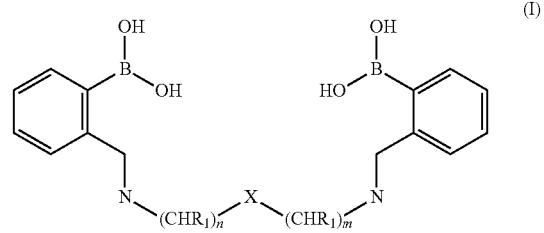

24 Claims, 2 Drawing Sheets

(56) References Cited

FOREIGN PATENT DOCUMENTS

| WO | 2011/101625 | 8/2011 |
|---|---|---|
| WO | 2011/101626 | 8/2011 |
| WO | 2011/101627 | 8/2011 |
| WO | 2011/101628 | 8/2011 |

OTHER PUBLICATIONS

Arimori et al., "Modular fluorescence sensors for saccharides," *Chem. Commun.*, 2001, 1836-1837.

Loim and Kelbyscheva, "Synthesis of dendrimers with terminal formyl groups," *Russian Chemical Bulletin,* Sep. 2004, 53:2080-2085.

Pangborn et al., "Safe and Convenient Procedure for Solvent Purification," *Organometallics,* 1996, 1518-1520.

Spry et al., "Deprotonation Dynamics and Stokes Shift of Pyranine (HPTS),"*J. Phys. Chem. A,* 2007, 11:230-237.

Still et al., "Rapid Chromatographic Technique for Preparative Separations with Moderate Resolution," *J. Org. Chem.*, 1978, 43:2923-2925.

Varedian et al., "An unexpected triethylsilan-triggered rearrangement of thioaurones to thioflavonols under SPPS conditions," *Tetrahedrons Letters,* 2008, 49:6033-6035.

\* cited by examiner (Compound 18)

(Compound 20)

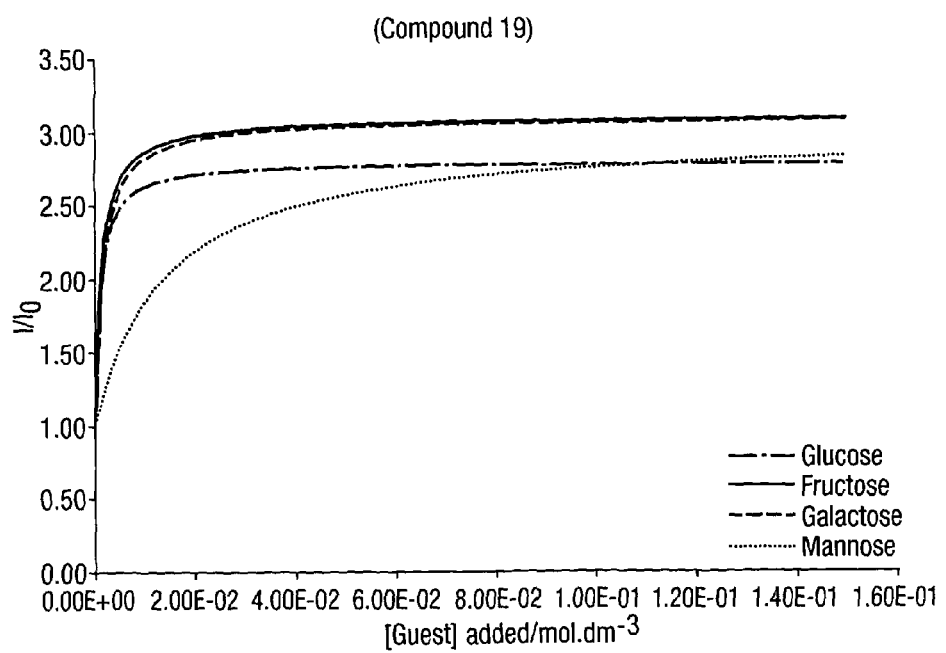

GLUCOSE SENSOR MOLECULES

CROSS REFERENCE TO RELATED APPLICATIONS

This application is the U.S. national stage under 35 USC §371 of International Application Number PCT/GB2012/000018, filed on 10 Jan. 2012, which claims priority to U.S. Application No. 61/431,756, filed on 11 Jan. 2011, the entire contents of which is hereby incorporated by reference.

The invention relates to glucose sensors containing a glucose receptor having a particular glucose binding site. Glucose sensor molecules containing the glucose binding site are also provided.

BACKGROUND TO THE INVENTION

The monitoring of glucose levels is of vital importance in the clinical setting. In particular, the regular monitoring of tissue glucose concentrations by diabetic patients and the care of hypoglycemic patients in an intensive care environment require simple and reliable methods for monitoring glucose levels. Such glucose monitoring has usually been based on electrochemical technology and glucose selective enzymes such as glucose oxidase. Sensors based on this technology are susceptible to denaturing of the enzyme, particularly in a biological environment. Further, because they are consumptive of glucose and rely on constant diffusion of glucose to the sensor electrodes, they are susceptible to errors and drift.

An alternative technology to the electrochemical devices is the use of optical sensors, such as those based on fluorescence intensity measurements. For instance, reversible, non-consumptive fluorescent optical sensors utilizing fluorophore boronic acid chemistries as the indicator for glucose have been developed. Such sensors measure the change in the emitted fluorescent intensity as a means of determining glucose concentration. Such boronic acid glucose indicating chemistries have the advantage of being reversible with glucose, non-consumptive and are more stable than the enzymes, such as glucose oxidase, which are commonly used in electrochemical glucose sensors. They can also be readily immobilized, within a hydrogel, onto an optical fibre.

These sensors rely on the selective binding of glucose to the boronic acid binding site. Boronic acids, however, are capable of binding other saccharides, for example galactose and fructose. An effective sensor should therefore provide good selectivity for glucose over other saccharides.

SUMMARY OF THE INVENTION

The present invention provides a glucose sensor having a particular glucose binding site which has been found to have a high selectivity for glucose over other saccharides. Sensors selective for glucose and other saccharides have been previously disclosed, for example in U.S. Pat. No. 6,387,672. U.S. Pat. No. 6,387,672 describes sensors having a binding site of formula:

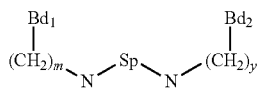

wherein the $Bd_1$ and $Bd_2$ groups are binding groups such as boronic acids and Sp represents an aliphatic spacer. The length of the carbon chain in the aliphatic spacer is selected to match the nature of the analyte. For binding to glucose, U.S. Pat. No. 6,387,672 teaches the use of a straight chain 6-carbon atom aliphatic spacer which is said to provide good selectivity for glucose.

The present inventors, however, have found that the selectivity of the binding site for glucose can be further improved by altering the 6-carbon atom aliphatic spacer. The present invention therefore provides a glucose sensor comprising a glucose receptor having a binding site of formula (I):

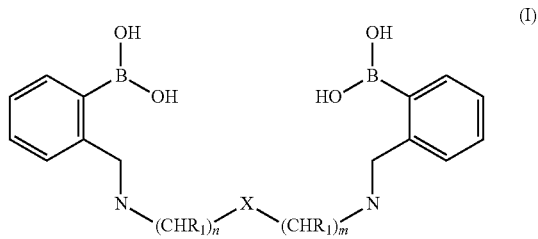

wherein X represents O, S, $NR_2$ or $CHR_3$;
n is from 1 to 4;
m is from 1 to 4, and n+m is 5;
$R_2$ represents hydrogen or $C_{1-4}$ alkyl;
each $R_1$ is the same or different and represents hydrogen, $C_{1-4}$ alkyl or $C_{3-7}$ cycloalkyl;
or $R_1$, together with an adjacent $R_1$, $R_2$ or $R_3$ group and the carbon or nitrogen atoms to which they are attached, form a $C_{3-7}$ cycloalkyl or a 5- or 6-membered heterocyclyl group,
wherein when X represents $CHR_3$, $R_3$ together with an adjacent $R_1$ group and the carbon atoms to which they are attached form a $C_{3-7}$ cycloalkyl group.

Particularly preferred receptors are those wherein X represents O, S or $NR_2$, preferably O or NH, in particular O.

Also provided is a glucose sensor molecule of formula (II):

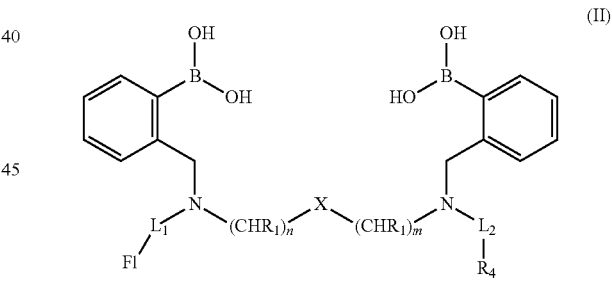

wherein X, n, m and $R_1$ are as defined above;
Fl is a fluorophore;
$L_1$ and $L_2$ are the same or different and represent a linker; and
$R_4$ is a support material, a hydrogen atom or an anchor group suitable for attaching the sensor molecule to a support material.

The present invention also provides a process for the preparation of a glucose sensor molecule as set out above, which process comprises reductive amination of (III) in the presence of (IV), followed by deprotection of the boronic acid group and optionally deprotection of $R_4$:

$$Fl\text{-}L_1\text{-}NH\text{---}(CHR_1)_n\text{---}X\text{---}(CHR_1)_m\text{---}NH\text{-}L_2\text{-}R_4 \quad (III)$$

wherein X, n, m, $R_1$ Fl, $L_1$ and $L_2$ are as defined above; and $R_4$ is a hydrogen atom or an anchor group suitable for attaching the sensor molecule to a support material, wherein $R_4$ is optionally protected by a protecting group;

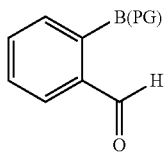

(IV)

wherein B(PG) is a boronic acid group protected by a protecting group.

Also provided is a method of detecting or quantifying the amount of glucose in an analyte, the method comprising contacting the analyte with a glucose receptor comprising a binding site of formula (I):

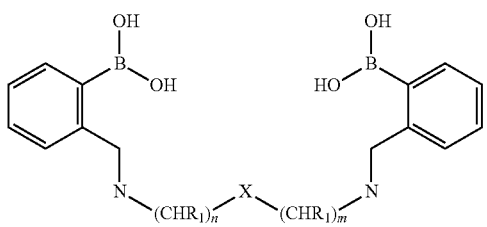

(I)

wherein X, n, m and $R_1$ are as defined above.

BRIEF DESCRIPTION OF THE FIGURES

FIGS. 2 and 3 provide similar graphs of the relative fluorescence intensity versus carbohydrate concentration for two comparative compounds.

DETAILED DESCRIPTION OF THE INVENTION

Figure 1:
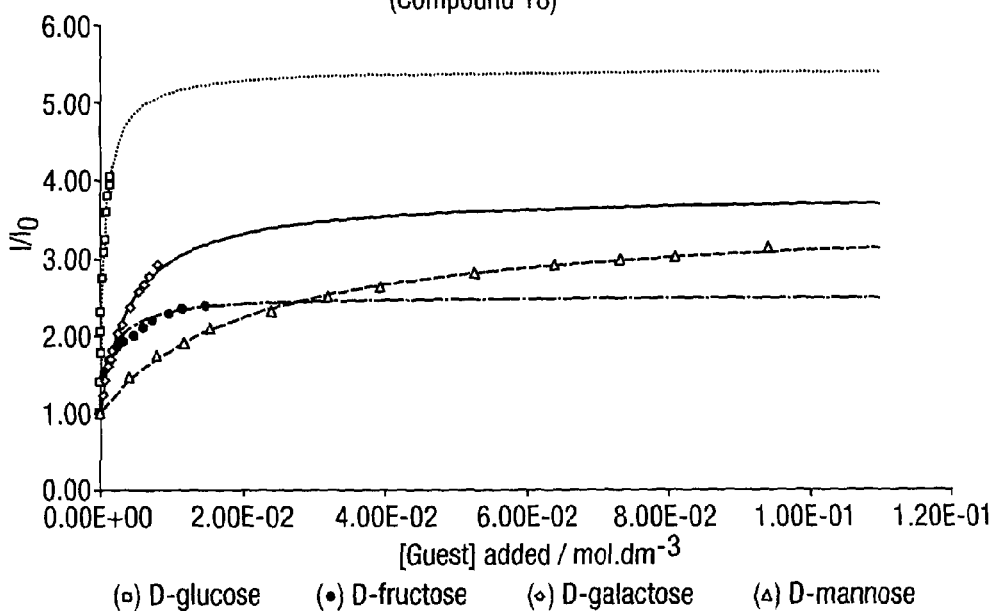
FIG. 1 provides a graph of the relative fluorescence intensity versus carbohydrate concentration for glucose sensor compound 18 of the invention in the presence of D-glucose, D-fructose, D-galactose and D-mannose.

As used herein a $C_{1-4}$ alkyl group may be a straight chain or branched alkyl group, for example a t-butyl, n-butyl, i-propyl, n-propyl, ethyl or methyl group, e.g. ethyl or methyl. $C_{1-4}$ alkyl groups are typically unsubstituted.

As used herein a $C_{1-6}$ alkylene group may be a straight chain or branched alkylene group, but is typically a straight chain alkylene group. A $C_{1-6}$ alkylene group is typically a $C_{1-4}$ alkylene group, for example n-butylene, n-propylene, ethylene or methylene, e.g. ethylene or methylene. $C_{1-6}$ alkylene groups are typically unsubstituted.

As used herein a $C_{3-7}$ cycloalkyl group is typically a cyclopentyl or cyclohexyl group. $C_{3-7}$ cycloalkyl groups may be unsubstituted or substituted. Suitable substituents are $C_{1-4}$ alkyl groups, for example methyl and ethyl. Preferably, a $C_{3-7}$ cycloalkyl group is unsubstituted.

As used herein a 5- or 6-membered heterocyclyl group is a 5- or 6-membered saturated ring containing one or more, typically one or two, e.g. one, heteroatom selected from N, O and S. Preferred heterocyclyl groups are those containing a nitrogen atom, for example piperidinyl and pyrrolidinyl. Heterocyclyl groups may be unsubstituted or substituted. Suitable substituents are $C_{1-4}$ alkyl groups, for example methyl and ethyl. Preferably, a heterocyclyl group is unsubstituted.

As used herein an arylene group is an unsaturated group which may be monocyclic, bicyclic, or which may contain three or four fused rings. Typically, an arylene group is phenylene. Arylene groups may be unsubstituted or substituted. Suitable substituents are $C_{1-4}$ alkyl groups, for example methyl and ethyl. Preferably, an arylene group is unsubstituted.

The present invention relates to glucose sensors, in particular fluorescent sensors. The sensor comprises a glucose receptor having a binding site having two boronic acid groups separated by a specific spacer group. Glucose present in the analyte binds to the boronic acid groups and forms a 1:1 complex with the receptor.

In the case of a fluorescent sensor, the sensor also comprises a fluorophore which is associated with the glucose receptor. Where a fluorophore is associated with the receptor, this indicates that binding of a glucose molecule to the receptor perturbs the fluorescence of the fluorophore, e.g. its wavelength, intensity or lifetime. Typically, in the absence of glucose, the receptor acts to quench the fluorescence of the fluorophore. However, where glucose is bound to the fluorophore, fluorescence quenching no longer occurs so that the intensity of the fluorescence is increased. Such fluorescent sensors therefore exhibit a change in wavelength, intensity and/or lifetime of the fluorescence when glucose binds to the binding site. Thus, the sensor may detect or quantify the amount of glucose present in the analyte by monitoring changes in the wavelength, intensity and/or lifetime of the fluorescence. Typically, the intensity or the lifetime is measured.

The glucose binding site of the present invention comprises a spacer between the two nitrogen atoms which is chosen to provide improved selective binding to glucose. The spacer has the formula:

—(CHR$_1$)$_n$—X—(CHR$_1$)$_m$—

X represents either a heteroatom selected from O, S or NR$_2$ or X may represent CHR$_3$. Typically, X represents O, S or NR$_2$, preferably X represents O.

The spacer is a 6-membered chain. Therefore, whilst n and m may vary between 1 and 4, the total n+m is always 5. Preferably, n is 2 or 3 and m is 2 or 3.

Typically, each $R_1$ is the same or different and is selected from hydrogen, $C_{1-4}$ alkyl and $C_{3-7}$ cycloalkyl, preferably from hydrogen and $C_{1-4}$ alkyl, more preferably from hydrogen, methyl and ethyl. Most preferably $R_1$ is hydrogen. The spacer group contains five $R_1$ groups. Typically, at least four of the $R_1$ groups represent hydrogen. In a preferred embodiment, all $R_1$ groups are the same and represent hydrogen.

In one embodiment, the spacer comprises a cyclic group. In this embodiment, $R_1$, together with an adjacent $R_1$, $R_2$ or $R_3$ group and the carbon or nitrogen atoms to which they are attached, form a $C_{3-7}$ cycloalkyl or 5- or 6-membered heterocyclyl group. The binding site in this embodiment is typically of formula (Ia):

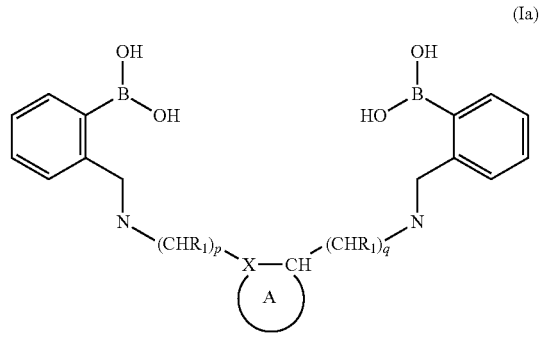

(Ia)

wherein p is from 1 to 4;
q is from 0 to 3, and p+q is 4;
X is N or CH, preferably X is N;
each $R_1$ is the same or different and represents hydrogen, $C_{1-4}$ alkyl or $C_{3-7}$ cycloalkyl; and
ring A is a $C_{3-7}$ cycloalkyl group or a 5- to 7-membered heterocyclyl group.

In formula (Ia), typically, each $R_1$ is the same or different and is selected from hydrogen, $C_{1-4}$ alkyl and $C_{3-7}$ cycloalkyl, preferably from hydrogen and $C_{1-4}$ alkyl, more preferably from hydrogen, methyl and ethyl. Most preferably $R_1$ is hydrogen. Preferably, at least 3 of the $R_1$ groups present represent hydrogen. More preferably, all $R_1$ groups are the same and represent hydrogen.

In formula (Ia), preferably p is 2 or 3 and q is 1 or 2, and p+q is 4.

When X is N, ring A typically forms a 5- or 6-membered heterocyclyl group, typically a piperidinyl or pyrrolidinyl group. When X is CH, ring A typically forms a $C_{3-7}$ cycloalkyl group, preferably cyclopentyl or cyclohexyl.

The cycloalkyl and heterocyclyl groups may be unsubstituted or substituted. Suitable substituents are $C_{1-4}$ alkyl groups. Preferably, the cycloalkyl and heterocyclyl groups are unsubstituted.

In a particularly preferred embodiment, in the binding site of formula (I):
X represents O;
n is from 1 to 4;
m is from 1 to 4 and n+m is 5; and
each $R_1$ represents hydrogen.

In a more preferred embodiment, in the binding site of formula (I):
X represents O;
n is 2 or 3, m is 2 or 3 and n+m is 5; and
each $R_1$ represents hydrogen.

Thus, particularly preferred binding sites of formula (I) are those of formula (I') and (I''), with (I'') being most preferred:

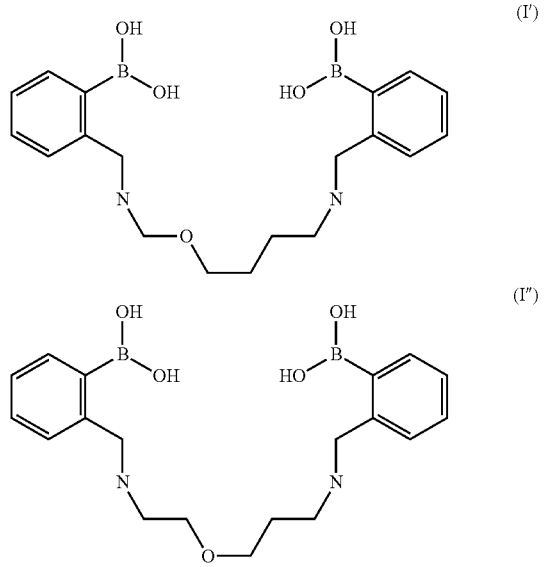

The two nitrogen atoms in the receptor marked as N* below:

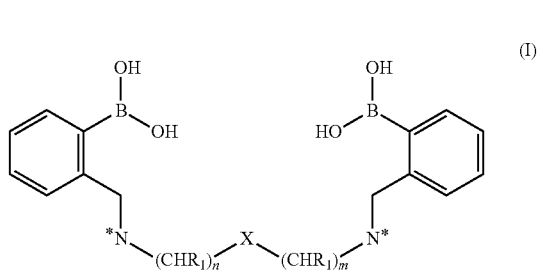

may either bear a hydrogen atom or may be connected to further moieties, e.g. to a fluorophore or to a support material. The moieties bonded to the two nitrogen atoms may be the same or different, but are typically different.

The receptor may be bonded via one of the nitrogen atoms to a support material. A support material as used herein is a molecule or substance to which the receptor can be tethered. The support material typically serves to immobilise or to restrict the movement of the receptor within the sensor. In one embodiment, the support material is a solid or gel-like support material such as a polymeric matrix. This can be used to physically immobilise the receptor in the desired position within the sensor. A hydrogel (a highly hydrophilic cross-linked polymeric matrix such as a cross-linked polyacrylamide) is an example of a suitable polymeric matrix.

In an alternative embodiment, the support material may be a water-soluble polymer or other water-soluble molecule such that the receptor-support material complex is itself water-soluble. Such a water-soluble complex may be provided in aqueous solution within the sensor. Examples of suitable water-soluble polymers include linear or lightly cross-linked polyacrylamides or polyvinyl alcohols. Other water-soluble molecules which can be used as the support material include dendrimers, cyclodextrins, cryptans and crown ethers. Dendrimers are preferred.

The sensor typically comprises a membrane to restrict or prevent the leakage of the receptor out of the sensor, but which allows glucose to enter the sensor. Dialysis membranes are suitable for this purpose. The use of a water-soluble support material serves to increase the molecular weight of the receptor and may also increase its water-solubility. The increase in molecular weight assists in restricting the passage of the receptor through the membrane and thereby restricts the movement of the receptor. The support material is typically of high molecular weight, for example at least 1000, preferably at least 2000, 5000 or 10,000.

Linkers may be used to connect the receptor to the support material. Examples of suitable linkers are alkylene or arylene groups, or combinations thereof, as described further below.

The presence of a support material on one of the nitrogen atoms is not essential. For example, where the receptor is itself water-soluble and of sufficiently high molecular weight that it does not pass through a dialysis membrane, no further attachment of support material is needed. In this case, the nitrogen atom may carry a hydrogen atom, or a linker group as described below terminating in a hydrogen atom.

In a preferred embodiment of the invention, the receptor is bonded to a fluorophore moiety to provide a glucose sensor molecule of formula (II):

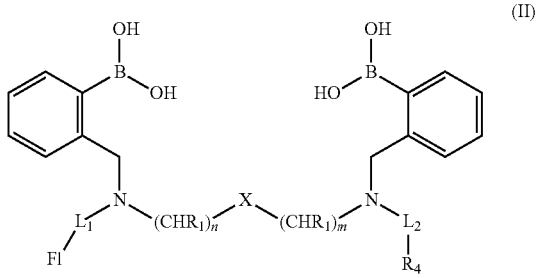

(II)

wherein X, n, m and $R_1$ are as defined above.

Fl represents a fluorophore group. The fluorophore may be selected from a broad range of different functional groups. Examples of suitable fluorophore groups include those having π-electron systems, for example naphthyl, anthryl, pyrenyl, phenanthryl and perylenyl and derivatives thereof. Pyrenyl and anthryl, in particular pyrenyl groups and their derivatives are preferred. Examples of suitable derivatives of these fluorophores include those having one or more sulphonyl substituents, for example two or three sulphonyl substituents, in particular those described in WO 2010/116142, the contents of which are incorporated herein by reference.

The fluorophore is linked to the receptor via a linking group, $L_1$. Typically $L_1$ consists of one or more alkylene groups, preferably $C_{1-6}$ alkylene groups, and/or one or more arylene groups. The $C_{1-6}$ alkylene group is typically a straight chain group. It is typically unsubstituted. Preferred $C_{1-6}$ alkylene groups are straight chain $C_{1-4}$ alkylene groups, e.g. methylene and ethylene, in particular methylene. The arylene group is typically a phenylene group. It is typically unsubstituted. In one embodiment, $L_1$ is a straight chain, unsubstituted $C_{1-4}$ alkylene group, more preferably methylene or ethylene, most preferably methylene.

In the above formula (II), one nitrogen atom of the receptor is bonded to a linker $L_2$. $L_2$ typically consists of one or more alkylene groups, preferably $C_{1-6}$ alkylene groups, and/or one or more arylene groups. The $C_{1-6}$ alkylene group is typically a straight chain group. It is typically unsubstituted. Preferred $C_{1-6}$ alkylene groups are straight chain $C_{1-4}$ alkylene groups, e.g. methylene and ethylene, in particular methylene. The arylene group is typically a phenylene group. It is typically unsubstituted.

In one aspect, the group $L_2$ is selected from -alkylene-, -alkylene-arylene- and -alkylene-arylene-alkylene. For example, $L_2$ may be a group of formula —($C_{1-2}$ alkylene)-Ph-($C_{0-2}$ alkylene)-, preferably methylene-phenylene-methylene-.

$R_4$ typically represents a support material such as a hydrogel or a dendrimer as described above. Alternatively, $R_4$ may be an end group such as a hydrogen atom, where no support material is present.

In a further embodiment, $R_4$ represents an anchor group suitable for attaching the molecule to a support material. Thus, in this embodiment, the invention provides a precursor for the final support material-receptor complex described above. The anchor group is typically a reactive group which is capable of forming a covalent bond with a second reactive group on, for example, the support material to which it is to be attached. Suitable anchor groups include alkene, ester, aldehyde, amine and azide groups. These anchor groups may alternatively be protected groups, e.g. protected aldehyde, amine or azide groups. Where an anchor group is present at position $R_4$, this may be used to react with a support material (optionally after deprotection) to provide a modified glucose sensor molecule wherein $R_4$ represents the support material.

Examples of preferred glucose sensor molecules of formula (II) are:

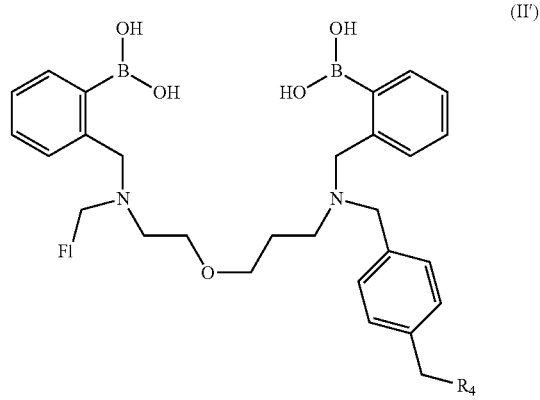

(II')

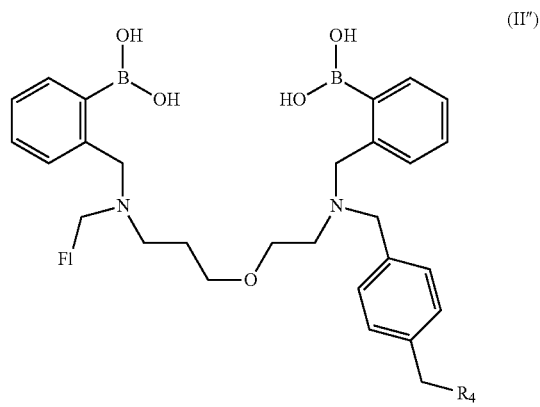

(II")

wherein Fl is a fluorophore as defined above, and $R_4$ is a support material, an anchor group suitable for attaching the molecule to a support material, or a hydrogen atom. Preferably, Fl is pyrene or a derivative thereof and $R_4$ is a support material or an anchor group selected from aldehyde, alkene, ester, azide or amine.

The glucose sensor molecules of the present invention can be prepared according to Scheme 1 below. Scheme 1 provides an exemplary synthesis in which X is O and $R_4$ is an anchor group.

Scheme 1, X = O

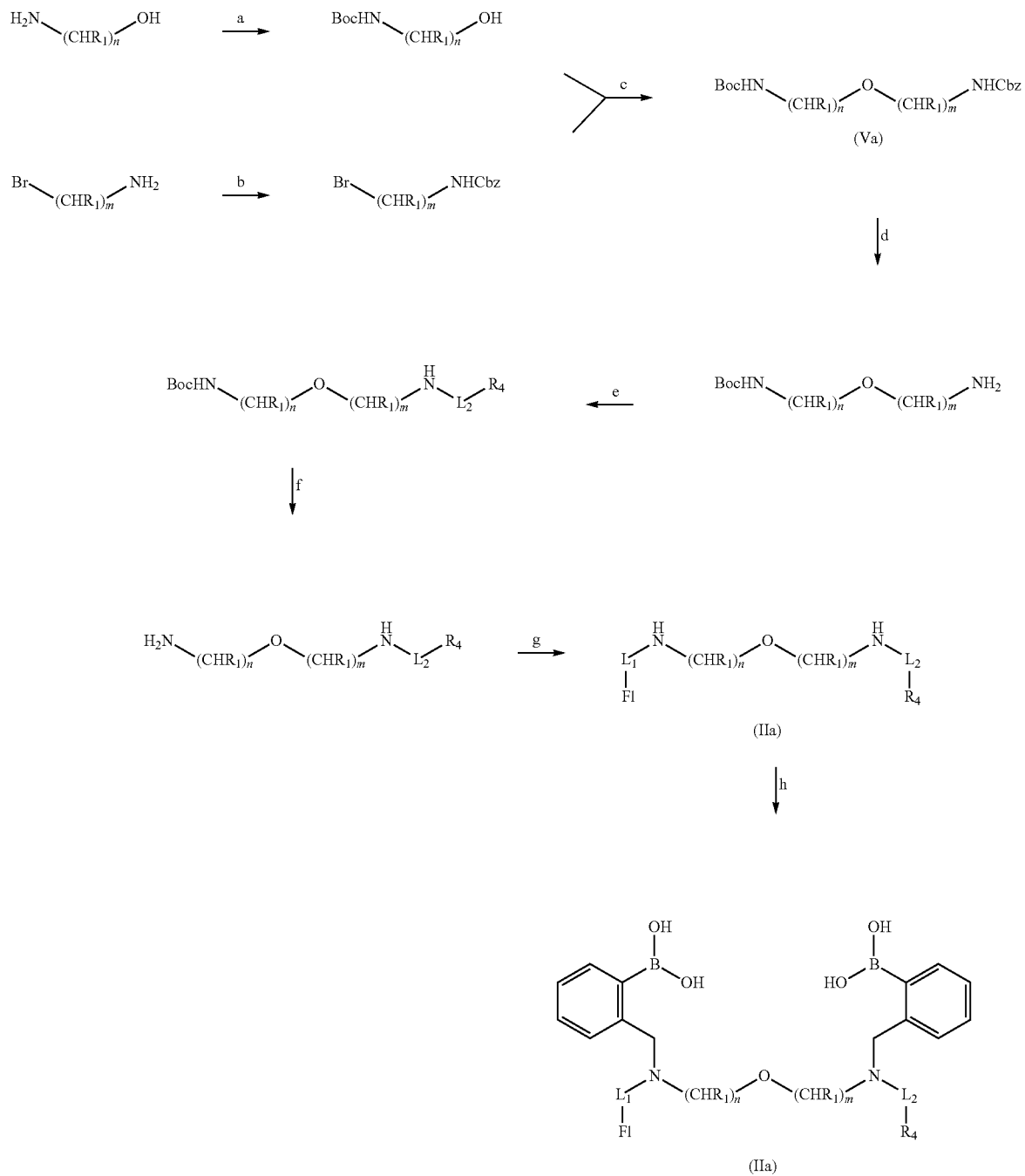

In steps (a) and (b), the amine groups are protected with different protecting groups. Here Boc and Cbz are exemplified, but alternative protecting groups could be used, as long as the synthesis uses different protecting groups at each amine. A Williamson ether type reaction is then carried out in step (c). Exemplary reaction conditions for steps (a) to (c) are as follows: a) 2-Ethanolamine, $Boc_2O$, DCM; b) 3-bromopropylamine hydrobromide, benzyl chloroformate, 15% aqueous NaOH; c) $^tBu_4NI$, 20% aqueous NaOH, DCM.

The di-protected molecule (Va) then undergoes successive deprotection and reductive amination in steps (d) to (h) to yield the final glucose sensor molecule (IIa). Exemplary reaction conditions are as follows: d) Pd/C, THF/MeOH sat. $NH_3$, $H_2$; e) activated -$L_2$-$R_4$ (e.g. compound 1, 4 or 8 described below), MeOH, ii) $NaBH_4$; f) TFA, DCM, 0° C.; g) i) activated Fl-$L_1$- (e.g. Pyrene-1-carboxaldehyde), MeOH/THF, ii) $NaBH_4$; h) i) potassium 2-formylphenyltrifluoroborate, $NaBH(OAc)_3$, DIPEA, THF, ii) LiOH, $MeCN/H_2O$ %.

Scheme 2 below depicts an alternative synthesis of the compounds of the invention in which X is NH:

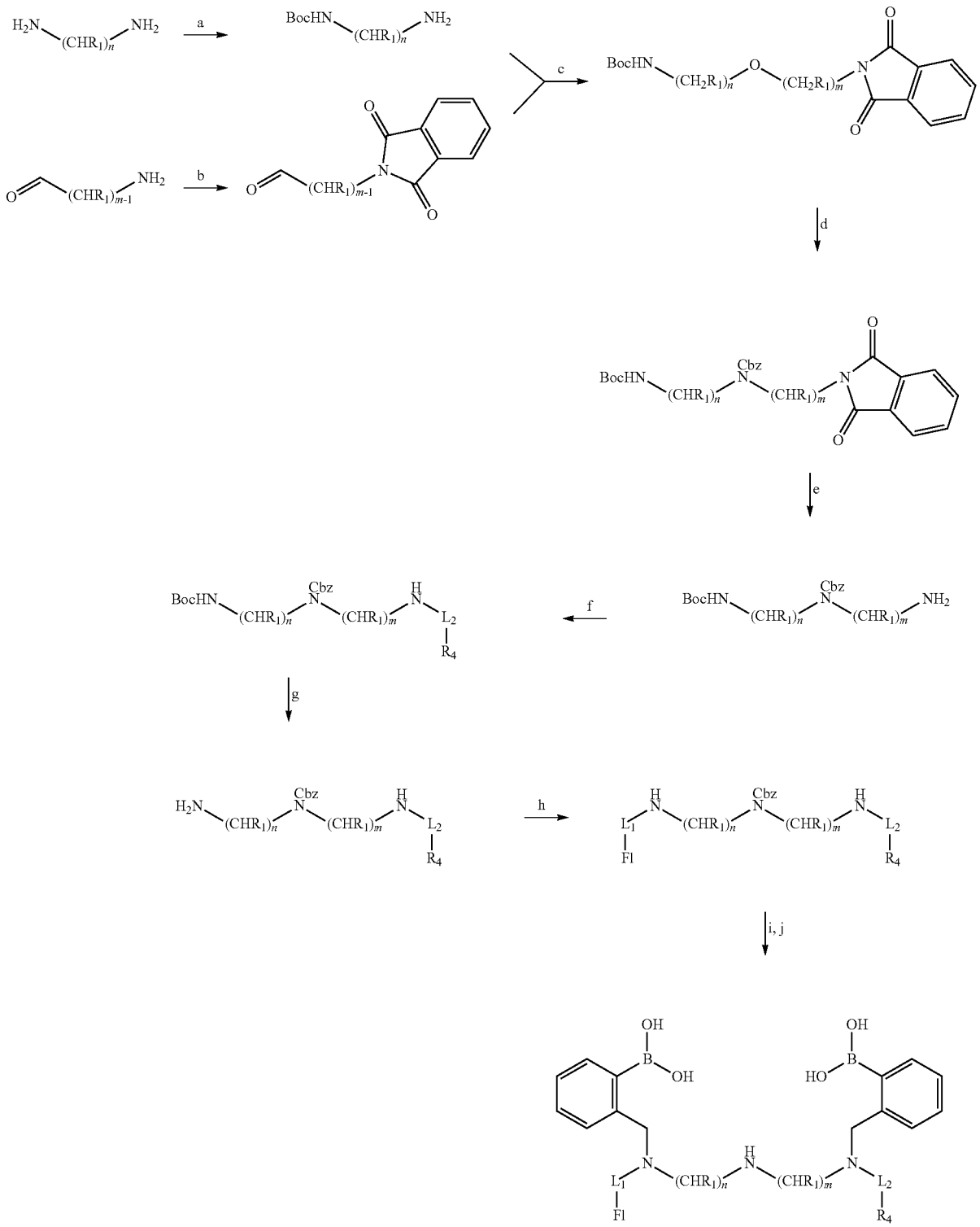

Scheme 2, X = NH a) Boc₂O, DCM; b) Potassium phthamide, DMF; c) i) MeOH, ii) NaBH₄; d) Benzyl chloroformate, DIPEA, THF; e) Hydrazine, DCM/MeOH, reflux; f) activated ——L₂—R₄ (e.g. compound 1, 4 or 8 described below), MeOH, ii) NaBH₄; g) TFA, DCM, 0° C.; h) i) activated Fl—L₁— (e.g. Pyrene-1-carboxaldehyde), MeOH/THF, ii) NaBH₄; i) i) potassium 2-formylphenyltrifluoroborate, NaBH(OAc)₃, DIPEA, THF, ii) LiOH, MeCN/H₂O%; j) Pd/C, H₂, THF/MeOH sat. NH₃.

The skilled person would be able to adapt the above schemes to provide the corresponding compounds in which X is S, X is NR$_2$, wherein R$_2$ is other than H or wherein X is CHR$_3$. For sensors in which R$_1$ forms a ring together with R$_2$ or R$_3$, for example the compounds of formula (Ia), scheme 2 can be adapted by replacing

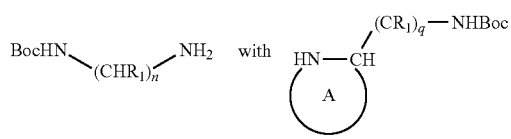

The activated Fl-L$_1$-compound is typically a compound in which the terminal carbon atom in an alkylene chain or arylene group of L$_1$ bears a reactive group capable of reacting with an amine. Aldehyde is an example of such a reactive group. Activated Fl-L$_1$-compounds are commercially available or could be prepared by the skilled person using techniques known in the art.

Schemes 3 and 4 below provide an exemplary synthesis of activated -L$_2$-R$_4$ compounds wherein L$_2$ is methylene-phenylene-methylene and R$_4$ is an anchor group. Compounds 1, 4 and 8 are each examples of suitable activated -L$_2$-R$_4$ compounds in which the anchor group R$_4$ is a protected aldehyde 1, an alkene 27, a protected amine 8 or azide 4.

Scheme 4

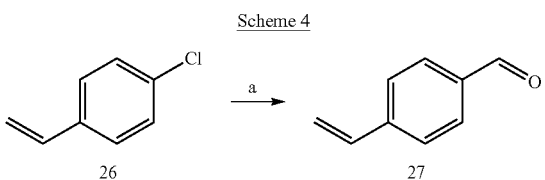

a) i) Mg, THF, EtBr, Δ; ii) DMF, 70%.

Further detail regarding the synthesis of an exemplary glucose sensor compound of the invention is provided in Example 1.

The above synthetic schemes provide glucose sensor compounds having an anchor group at R$_4$. The skilled person would be able to provide suitable alternative starting materials in order to provide corresponding glucose sensor compounds having a hydrogen atom at R$_4$. In order to provide a support material at R$_4$, the compounds of formula (II) having an anchor group are reacted with an activated support material. The activated support material has a reactive group capable of forming a bond with the anchor group (e.g. an amine group).

The present invention also provides a method of detecting or quantifying the amount of glucose in an analyte, the method comprising contacting the analyte with a glucose Scheme 3

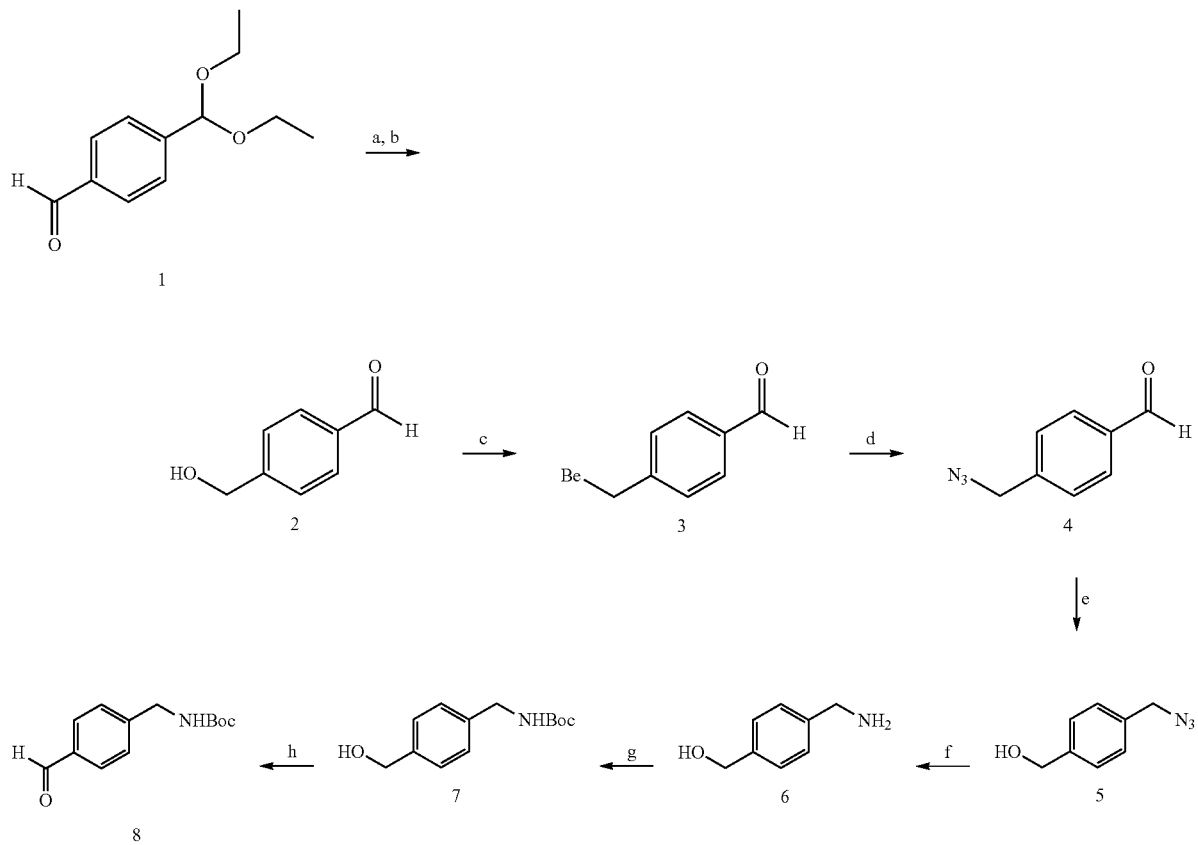

a) NaBH$_4$, MeOH; b) THF, 2M HCl; c) HBr in acetic acid, DCM; d) NaN$_3$, DMF, 60° C.; e) NaBH$_4$, MeOH, 0° C.; f) PPh$_3$, H$_2$O, 60° C.; g) Boc$_2$O, CHCl$_3$, 88%; h) MnO$_2$, DCM.

receptor having a binding site of formula (I) as set out above. Typically, the analyte is contacted with a glucose sensor compound of formula (Ia) as set out above, in particular a glucose sensor compound of formula (Ia) in which R is a hydrogen atom or a support material. The glucose in the analyte binds to the binding site in a selective manner. The binding of glucose causes a perturbation of the fluorescence of the fluorophore which can be detected. This can be achieved by detecting a change in the intensity of the fluorophore, or by detecting a change in the lifetime of the fluorophore.

The present invention is described below with reference to particular Examples. The invention is not intended to be limited to these particular Examples.

EXAMPLES

Example 1

Synthesis of Glucose Sensor Molecule 1.1 1-(Diethoxymethyl)-4-(hydroxymethyl)benzene, 1

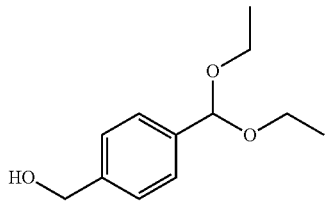

4-(Diethoxymethyl)benzaldehyde (10 g, 48 mmol) was dissolved in methanol (200 ml) and cooled to 0° C. NaBH$_4$ (4.54 g, 120 mmol, 2.5 eq) was then added slowly and the reaction mixture was stirred for 1 hour, after which the solvent was evaporated. The residue obtained was dissolved in ethyl acetate (100 ml) and water (100 ml), the phases were separated and the organic phase was washed with water (100 ml), dried over magnesium sulphate, and evaporated to yield 1 as a clear oil (10.09 g, 48 mmol, 100%). $^1$H NMR (300 MHz, CDCl$_3$) δ=7.48 (d, $^3$J(H,H)=8.1 Hz, 2H, ArCH α to CH$_2$OH), 7.37 (d, $^3$J(H,H)=8.1 Hz, 2H, ArCH α to CH(OEt)$_2$), 5.51 (s, 1H, CH(OEt)$_2$), 4.70 (d, $^3$J(H,H)=5.9 Hz, 2H, CH$_2$OH), 3.61 (dq, $^3$J(H,H)=7.1 Hz, $^2$J(H,H)=9.5 Hz, 2H, CH$_2$CH$_3$), 3.56 (dq, $^3$J(H,H)=7.1 Hz, $^2$J(H,H)=9.5 Hz, 2H, CH$_2$CH$_3$), 1.75 (t, $^3$J(H,H)=5.9 Hz, 1H, CH$_2$OH), 1.24 (t, $^3$J(H,H)=7.1 Hz, 6H, CH$_2$CH$_3$); $^{13}$C NMR (75 MHz, CDCl$_3$) δ=140.9 (ArCCH$_2$OH), 138.6 (ArCCH(OEt)$_2$), 126.9 (ArCH α to ArCCH$_2$OH), 126.8 (ArCH α to ArCCH(OEt)$_2$), 101.3 (CH(OEt)$_2$), 65.1 (CH$_2$OH), 61.0 (OCH$_2$CH$_3$), 15.2 (OCH$_2$CH$_3$).

1.2 4-(Hydroxymethyl)benzaldehyde, 2

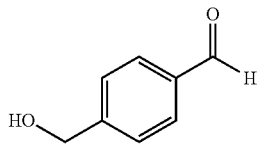

Alcohol 1 (10.09 g, 48 mmol) was dissolved in a mixture of THF (100 ml) and 2 M HCl (100 ml) and stirred for 1 hour. The solvent was evaporated and the residue obtained was dissolved in ethyl acetate (100 ml) and water (100 ml). The phases were separated and the organic phase was washed with water (100 ml), dried over magnesium sulphate, and evaporated to yield 2 as a white solid (6.54 g, 48 mmol, 100%). R$_f$=0.54 (ethyl acetate/chloroform, 1:1); ν$_{max}$=3327, 1689, 1607, 1206, 1010, 823 cm$^{-1}$; $^1$H NMR (250 MHz, CDCl$_3$) δ=10.02 (s, 1H, CHO), 7.89 (d, $^3$J(H,H)=8.1 Hz, 2H, ArCH α to CHO), 7.54 (d, $^3$J(H,H)=8.1 Hz, 2H, ArCH α to CH$_2$OH), 4.82 (d, $^3$J(H,H)=5.9 Hz, 2H, CH$_2$OH), 1.94 (t, $^3$J(H,H)=5.9 Hz, 1H, CH$_2$OH); $^{13}$C NMR (75 MHz, CDCl$_3$) δ=192.0 (CHO), 147.7 (ArCCOH), 135.7 (ArCCHO), 130.0 (ArCH α to ArCCHO), 127.0 (ArCH α to ArCCH$_2$OH), 64.6 (CH$_2$OH); HRMS (ESI$^-$): m/z calculated for C$_8$H$_7$O$_2$ [M-H]$^-$: 135.0446, found 135.0448; elemental analysis calcd (%) for C$_8$H$_8$O$_2$ (136.15): C, 70.57; H, 5.92. found: C, 70.70; H, 6.00.

1.3 4-(Bromomethyl)benzaldehyde, 3

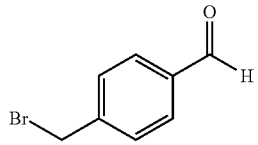

Alcohol 2 (6.46 g, 47.5) was dissolved in DCM (100 ml) before HBr in acetic acid (33 wt %, 42 ml, 243, 5 eq) was added and stirred overnight. Water (100 ml) was added to the reaction mixture and the phases were separated and the organic phase obtained was washed with a NaOH solution (2 M, 2×100 ml), dried over Na$_2$SO$_4$, and evaporated. The residue was washed through a silica plug to yield 3 as a white solid (9.04 g, 45.4 mmol, 95%). R$_f$=0.77 (DCM); m.p.=100° C. (recrystallised from hexane); ν$_{max}$=1682, 1604, 1209, 1200, 830, 770, 726 cm$^{-1}$; $^1$H NMR (300 MHz, CDCl$_3$) δ=10.02 (s, 1H, CHO), 7.87 (d, $^3$J(H,H)=8.2 Hz, 2H, ArCH α to CHO), 7.56 (d, $^3$J(H,H)=8.2 Hz, 2H, ArCH α to CH$_2$Br), 4.52 (s, 21-1, CH$_2$Br); $^{13}$C NMR (75 MHz, CDCl$_3$) δ=191.5 (CHO), 144.2 (ArCCBr), 136.2 (ArCCHO), 130.2 (ArCH α to ArCCHO), 129.7 (ArCH α to ArCCH$_2$Br), 31.9 (CH$_2$Br); HRMS (ESI$^-$): m/z calculated for C$_8$H$_6$BrO [M-H]$^-$: 196.9602, found 196.9602; elemental analysis calcd (%) for C$_8$H$_7$BrO (199.04): C, 48.27; H, 3.54. found: C, 47.40; H, 3.53.

1.4 4-(Azidomethyl)benzaldehyde, 4

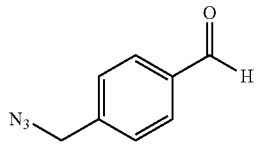

Bromide 3 (180 mg, 0.90 mmol) was dissolved in DMF (10 ml). Sodium azide (88 mg, 1.35 mmol) was added. The reaction mixture was then heated at 60° C. for an hour. The reaction mixture was allowed to cool and was dissolve in ethyl acetate (150 ml) and H$_2$O (150 ml). The phases were separated and the organic phase was washed again with water (2×150 ml). The organic phase was dried over sodium sulphate, and evaporated under reduced pressure to yield 4 as an oil (134 mg, 0.83 mmol, 92%). R$_f$=0.70 (DCM); ν$_{max}$=2094, 1694, 1607, 1207, 1167, 812, 773 cm$^{-1}$; $^1$H NMR (300 MHz, CDCl$_3$) δ=10.02 (s, 1H, CHO), 7.90 (d, $^3$J(H,H)=7.9 Hz, 2H, ArCH α to CHO), 7.48 (d, $^3$J(H,H)=7.9 Hz, 2H, ArCH α to CH$_2$N$_3$), 4.45 (s, 2H, CH$_2$N$_3$); $^{13}$C NMR (75 MHz, CDCl$_3$)

δ=191.6 (CHO), 142.1 (ArCCH₂N₃), 136.2 (ArCCHO), 130.2 (ArCH α to ArCCHO), 128.4 (ArCH α to ArCCH₂N₃), 54.2 (CH₂N₃); HRMS (ESI⁺): m/z calculated for C₈H₇N₃ONa [M+Na]⁺: 184.0481, found 184.0497.

1.5 1-(Azidomethyl)-4-(hydroxymethyl)benzene, 5

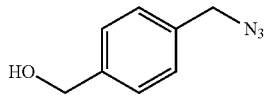

Azide 4 (2.0 g, 12.4 mmol) was dissolved in MeOH (50 ml) and cooled to 0° C. before NaBH₄ was added slowly and the reaction mixture was stirred for 1 hour, after which the solvent was evaporated. The residue obtained was dissolved in ethyl acetate (50 ml) and water (50 ml), the phases were separated and the organic phase was washed with water (100 ml), dried over Na₂SO₄, and evaporated to yield 5 as a clear oil (1.96 g, 12.0 mmol, 97%). $R_f$=0.45 (DCM); $v_{max}$=cm⁻¹; ¹H NMR (300 MHz, CDCl₃) δ=7.40 (d, ³J(H,H) 8.2 Hz, 2H, ArCH α to CH₂OH), 7.33 (d, ³J(H,H)=8.2 Hz, 2H, ArCH α to CH₂N₃), 4.71 (s, 2H, CH₂OH), 4.34 (s, 2H, CH₂N₃), 1.80 (bs, 1H, OH); ¹³C NMR (75 MHz, CDCl₃) δ=141.0 (ArCCH₂OH), 134.7 (ArCCH₂N₃), 128.5 (ArCH α to CH₂N₃), 127.4 (ArCH α to CH₂OH), 64.9 (CH₂OH), 54.5 (CH₂N₃).

1.6 1-(Aminomethyl)-4-(hydroxymethyl)benzene, 6

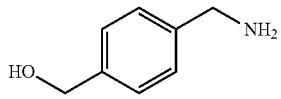

Azide 5 (1.96 g, 12.0 mmol) and PPh₃ (6.50 g, 24.8 mmol, 2.05 eq) were dissolved in THF (25 ml) and heated at 60° C. for 1 hour. Water (4.5 ml, 248 mmol, 20 eq) was added and the reaction was heated overnight. The solvent was evaporated and the residue obtained was purified by flash chromatography (eluent DCM to 4:1 DCM/methanol saturated with NH₃) to yield 6 as a white solid (1.44 g, 10.5 mmol, 85%). $R_f$=0.05 (9:1, DCM/MeOH sat. NH₃); $v_{max}$=cm⁻¹; ¹H NMR (300 MHz, CDCl₃) δ=7.35 (d, ³J(H,H)=8.4 Hz, 2H, ArCH α to CH₂NH₂), 7.30 (d, ³J(H,H)=8.4 Hz, 2H, ArCH α to CH₂OH), 4.67 (s, 2H, CH₂OH), 3.85 (s, 2H, CH₂NH₂), 1.68 (bs, 3H, OH, NH₂); ¹³C NMR (75 MHz, CDCl₃) δ=142.6 (ArCCH₂NH₂), 139.6 (ArCCH₂OH), 127.3 (ArCH), 127.2 (ArCH), 65.0 (CH₂OH), 46.2 (CH₂NH₂); HRMS (ESI⁺): m/z calculated for C₈H₁₂NO [M+H]⁺: 138.0913, found 138.0933.

1.7 1-ᵗButoxycarbonylaminomethyl-4-hydroxymethyl benzene, 7

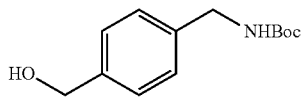

Amine 6 (1.44 g, 10.5 mmol) was dissolved in CHCl₃ (50 ml) and Boc₂O (2.29 g, 10.5 mmol, 1 eq) was added slowly. The reaction was stirred under nitrogen overnight before the solvent was evaporated and the residue obtained was dissolved in ethyl acetate (50 ml). This solution was washed with a citric acid solution (3×50 ml), brine (50 ml), dried over Na₂SO₄, and evaporated to yield 7 as a white solid (2.20 g, 9.2 mmol, 88%). $R_f$=0.57 (DCM/MeOH sat. NH₃, 8:2); $v_{max}$=cm⁻¹; ¹H NMR (300 MHz, CDCl₃) δ=7.33 (d, ³J(H,H)=8.2 Hz, 2H, ArCH α to CH₂OH), 7.26 (d, ³J(H,H)=8.2 Hz, 2H, ArCH α to CH₂NHBoc), 4.86 (bs, 1H, NHBoc), 4.68 (s, 2H, CH₂OH), 4.30 (d, ³J(H,H)=5.7 Hz, 2H, CH₂NHBoc), 1.96 (bs, 1H, OH), 1.46 (s, 9H, C(CH₃)₃); ¹³C NMR (75 MHz, CDCl₃) δ=155.9 (CO), 140.0 (ArCCH₂OH), 138.3 (ArCCH₂NHBoc), 127.6 (ArCH α to CH₂NHBoc), 127.2 (ArCH α to CH₂OH), 85.2 (C(CH₃)₃), 65.0 (CH₂OH), 44.4 (CH₂NHBoc), 28.4 (C(CH₃)₃); HRMS (ESI⁺): m/z calculated for C₁₃H₁₉NO₃Na [M+Na]⁺: 260.1257, found 260.1253.

1.8 4-ᵗButoxycarbonylaminomethyl-benzaldehyde, 8

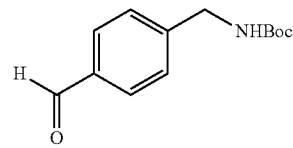

Alcohol 7 (2.20 g, 9.2 mmol) was dissolved in DCM (100 ml) and MnO₂ (8.18 g, 92 mmol, 10 eq) was added and the resulting suspension was stirred for 3 hours. The reaction mixture was then filtered through celite and evaporated to yield Error! Reference source not found. as a white solid (2.18 g, 9.2 mmol, 100%). $R_f$=0.62 (DCM/Ethyl acetate, 9:1); $v_{max}$=cm⁻; ¹H NMR (300 MHz, CDCl₃) δ=10.0 (CHO), 7.85 (d, ³J(H,H)=8.1 Hz, 2H, ArCH α to CHO), 7.45 (d, ³J(H,H)=8.1 Hz, 2H, ArCH α to CH₂NHBoc), 4.99 (bs, 1H, NHBoc), 4.40 (d, ³J(H,H)=5.7 Hz, 2H, CH₂NHBoc), 1.47 (s, 9H, C(CH₃)₃); ¹³C NMR (75 MHz, CDCl₃) δ=191.9 (CHO), 155.9 (CO), 145.9 (ArCCH₂NHBoc), 135.5 (ArCCHO), 130.1 (ArCH α to CHO), 127.6 (ArCH α to CH₂NHBoc), 85.1 (C(CH₃)₃), 44.3 (CH₂NHBoc), 28.3 (C(CH₃)₃); HRMS (ESI⁺): m/z calculated for C₁₃H₁₉NO₃Na [M Na]⁺: 258.1101, found 258.1094. NMR data consistent with published data.[6]

1.9 Potassium 2-Formylphenyltrifluoroborate, 10

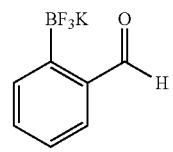

2-Formyl boronic acid (2.0 g, 13.3 mmol) was dissolved in MeOH (5 ml) before KHF₂ (4.16 g, 53.3 mmol) was added. A white precipitate formed and the solvent was evaporated 30 minutes after the addition of the KHF₂. The residue obtained was extracted with MeOH/acetone (1:4, 4×25 ml) and evaporated before being recrystalised from diethyl ether to yield 10 as a white crystalline solid (2.82 g, 13.3 mmol, 100%). ¹H NMR (300 MHz, DMSO-d₆) δ=10.44 (s, 1H, CHO), 7.67 (d, ³J(H,H)=7.4 Hz, 1H, ArCH), 7.61 (d, ³J(H,H)=7.4 Hz, 1H, ArCH), 7.39 (t, ³J(H,H)=7.4 Hz, 1H, ArCH (3), 7.23 (t, ³J(H,H)=7.4 Hz, 1H, ArCH); ¹¹B NMR (96 MHz, DMSO-d₆) δ=8.5; ¹³C NMR (75 MHz, DMSO-d₆) δ=197.0 (CHO), 132.8 (ArCH), 132.7 (ArCCHO), 131.9 (ArCH), 125.8

(ArCH), 124.4 (ArCH); HRMS (ESI+): m/z calculated for $C_7H_5OBF_3K$ [M–K]−: 173.0386, found 173.0396.

1.10 2-($^t$Butoxycarbonylamino)ethanol, 11

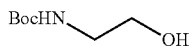

11

A solution of Boc$_2$O (33.6 g, 154 mmol, 1.1 eq) in dry DCM (40 ml) was added dropwise to a solution of 2-aminoethanol (8.55 g, 140 mmol) in dry DCM (180 ml) at r.t. under nitrogen. The reaction mixture was stirred overnight then washed with a saturated NaHCO$_3$ solution (3×200 ml). The organic layer was dried over Na$_2$SO$_4$ and evaporated. The oil obtained was distilled under reduced pressure to give 11 as a colourless clear oil (16.0 g, 99 mmol, 71%). $^1$H NMR (300 MHz, CDCl$_3$) δ=5.06 (bs, 1H, NHBoc), 3.67 (t, $^3$J(H,H)=5.1 Hz, 2H, CH$_2$OH), 3.26 (t, $^3$J(H,H)=5.1 Hz, 2H, CH$_2$NHBoc), 1.43 (s, 9H, C(CH$_3$)$_3$), 1.25 (s, 1H, CH$_2$OH); $^{13}$C NMR (75 MHz, CDCl$_3$) δ=156.8 (CO), 79.6 (C(CH$_3$)$_3$), 62.3 (CH$_2$OH), 43.2 (CH$_2$NHBoc), 28.3 (C(CH$_3$)$_3$); HRMS (ESI+): m/z calculated for $C_7H_{16}NO_3$ [M+H]+: 162.1130, found 162.1123, m/z calculated for $C_7H_{15}NO_3Na$ [M+Na]+: 184.0950, found 184.0942.

1.11 3-(Benzyloxycarbonylamino)propyl bromide, 12

12

3-Bromopropylamine hydrobromide (5.0 g, 22.8 mmol) was dissolved in an aqueous NaOH solution (15 wt %, 80 ml) and cooled to 0° C. under nitrogen before benzyl chloroformate was added dropwise. The reaction was left to stir overnight then ethyl acetate (100 ml) was added and the phases were separated. The organic phase was further washed with a HCl solution (2 M, 100 ml), a NaOH solution (2 M, 100 ml), brine (100 ml), dried over Na$_2$SO$_4$, and evaporated to yield 12 as a clear oil (6.22 g, 22.8 mmol, 100%). R$_f$=0.31 (8:2 Hexane/Ethyl acetate); $^1$H NMR (300 MHz, CDCl$_3$) δ=7.40-7.33 (m, 5H, ArCH), 5.11 (s, 2H, CH$_2$Ph), 4.94 (bs, 1H, NHCbz), 3.45 (t, $^3$J(H,H)=6.4 Hz, 2H, CH$_2$Br), 3.36 (q, $^3$J(H,H)=6.4 Hz, 2H, CH$_2$NHCbz), 2.08 (q, $^3$J(H,H)=6.4 Hz, 2H, CH$_2$CH$_2$CH$_2$); $^{13}$C NMR (75 MHz, CDCl$_3$) δ=156.4 (CO), 136.4 (ArCCH$_2$), 128.5 (ArCH), 128.2 (ArCH), 127.0 (ArCH), 66.8 (CH$_2$Ph), 39.4 (CH$_2$NHCbz), 32.4 (CH$_2$CH$_2$CH$_2$), 30.6 (CH$_2$Br); HRMS (ESI+): m/z calculated for $C_{11}H_{14}BrNO_2Na$ [M+Na]+: 294.0106, found 294.0099.

1.12 2-($^t$Butoxycarbonylamino)ethyl 3-(benzyloxycarbonylamino)propyl ether, 13

13

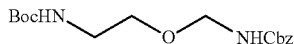

Alcohol 11 (1.0 g, 6.20 mmol), bromide 12 (2.19 g, 8.06 mmol, 1.3 eq), and $^t$BuNI (2.98 g, 8.06 mmol, 1.3 eq), were dissolved in DCM (50 ml) and an aqueous solution of NaOH (20 wt %, 50 ml) was added and the reaction was stirred overnight under nitrogen. The phases were separated and the aqueous phase was washed with DCM (2×50 ml), the organic phases were combined, dried over Na$_2$SO$_4$ and evaporated. The residue obtained was purified by flash chromatography (eluent DCM to ethyl acetate) to yield Error! Reference source not found. as a clear oil (568 mg, 1.61 mmol, 26%). R$_f$=0.34 (9:1 DCM/MeOH saturated with NH$_3$); $^1$H NMR (300 MHz, CDCl$_3$) δ=7.38-7.30 (m, 5H, ArCH), 5.13 (bs, 1H, NHX), 5.10 (s, 2H, CH$_2$Ph), 4.97 (bs, 1H, NHX), 3.48 (m, 4H, CH$_2$O), 3.30 (m, 4H, CH$_2$N), 1.77 (q, $^3$J(H,H)=6.1 Hz, 2H, CH$_2$CH$_2$CH$_2$), 1.44 (s, 9H, C(CH$_3$)$_3$); $^{13}$C NMR (75 MHz, CDCl$_3$) δ=156.4 (CO), 156.0 (CO), 136.6 (ArC), 128.5 (ArCH), 128.1 (ArCH), 128.0 (ArCH), 79.3 (C(CH$_3$)$_3$), 70.0 (BocHNCH$_2$CH$_2$O), 68.7 (OCH$_2$CH$_2$CH$_2$), 66.5 (CH$_2$Ph), 40.3 (CH$_2$NHBoc), 38.7 (CH$_2$CH$_2$CH$_2$NHCbz), 29.7 (CH$_2$CH$_2$CH$_2$), 28.4 (C(CH$_3$)$_3$); HRMS (ESI+): m/z calculated for $C_{18}H_{29}N_2O_5$ [M+H]+: 353.2071, found 353.2072, m/z calculated for $C_{18}H_{28}N_2O_5Na$ [M+Na]: 375.1890, found 375.1890.

1.13 2-($^t$Butoxycarbonylamino)ethyl 3-aminopropyl ether, 14

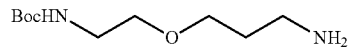

14

Pd on C (200 mg) was activated by heating at 300° C. under vacuum for 4 hours before a solution of ether 13 (568 g, 1.61 mmol) in THF and MeOH saturated with NH3 (1:1, 100 ml) was added. The flask was evacuated and filled with hydrogen (1 atm) and the reaction was stirred for 1 hour. The reaction mixture was then filtered over celite and washed with ethyl acetate before the filtrate evaporated. The residue obtained was purified by flash chromatography (eluent DCM to DCM/methanol saturated with NH$_3$, 19:1) to yield Error! Reference source not found. as a clear oil (334 mg, 1.57 mmol, 98%). R$_f$=0.65 (17:3 DCM/MeOH saturated with NH$_3$); $^1$H NMR (300 MHz, CDCl$_3$) δ=5.03 (bs, 1H, NHBoc), 3.48 (t, $^3$J(H,H)=5.3 Hz, 2H, OCH$_2$CH$_2$CH$_2$NH$_2$), 3.43 (t, $^3$J(H,H)=6.2 Hz, 2H, OCH$_2$CH$_2$NHBoc), 3.25 (q, $^3$J(H,H)=5.3 Hz, 2H, OCH$_2$CH$_2$NHBoc), 2.75 (t, $^3$J(H,H)=6.8 Hz, 2H, OCH$_2$CH$_2$CH$_2$NH$_2$), 1.67 (quintet, $^3$J(H,H)=6.5 Hz, 2H, OCH$_2$CH$_2$CH$_2$NH$_2$), 1.40 (s, 9H, C(CH$_3$)$_3$), 1.27 (bs, 2H, NH$_2$); $^{13}$C NMR (75 MHz, CDCl$_3$) δ=155.9 (CO), 79.0 (C(CH$_3$)$_3$), 69.7 (OCH$_2$CH$_2$NHBoc), 69.0 (OCH$_2$CH$_2$CH$_2$NH$_2$), 40.3 (OCH$_2$CH$_2$NHBoc), 39.4 (OCH$_2$CH$_2$CH$_2$NH$_2$), 33.2 (OCH$_2$CH$_2$CH$_2$NH$_2$), 28.3 (C(CH$_3$)$_3$); HRMS (ESI+): m/z calculated for $C_{10}H_{23}N_2O_3$ [M+H]+: 219.1703, found 219.1690.

1.14 2-($^t$Butoxycarbonylamino)ethyl 3-N-(4-(azidomethyl)benzyl)-aminopropyl ether, 15

15

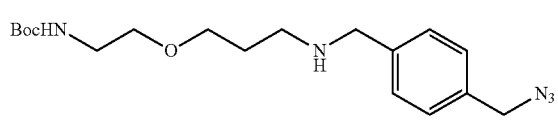

Amine 14 (270 mg, 1.24 mmol) and aldehyde 4 (219 mg, 1.36 mmol, 1.1 eq) were dissolved in methanol (50 ml) and stirred overnight. The reaction mixture was then cooled to 0° C. and NaBH$_4$ (117 mg, 3.1 mmol, 2.5 eq) was then added slowly and the reaction mixture was stirred for 2 hours, after which the solvent was evaporated. The residue obtained was dissolved in DCM (50 ml) and water (50 ml), the phases were separated and the aqueous phase was extracted with DCM (2×50 ml), dried over Na$_2$SO$_4$, and evaporated. The crude product was purified by flash chromatography (eluent DCM to DCM/methanol saturated with NH$_3$, 97:3) yielding 15 as a clear oil (360 mg, 0.99 mmol, 80%). R$_f$=0.63 (97:3 DCM/MeOH saturated with NH$_3$); $^1$H NMR (300 MHz, CDCl$_3$) δ=7.34 (d, $^3$J(H,H)=8.2 Hz, 2H, ArCH α to CH$_2$NH), 7.27 (d, $^3$J(H,H)=8.2 Hz, 2H, ArCH α to CH$_2$N$_3$), 5.03 (bs, 1H, NHBoc), 4.32 (s, 2H, CH$_2$N$_3$), 3.80 (s, 2H, CH$_2$NH), 3.52 (t, $^3$J(H,H)=6.2 Hz, 2H, OCH$_2$CH$_2$CH$_2$NH), 3.47 (t, $^3$J(H,H)=5.2 Hz, 2H, OCH$_2$CH$_2$NHBoc), 3.29 (q, $^3$J(H,H)=5.3 Hz, 2H, OCH$_2$CH$_2$NHBoc), 2.71 (t, $^3$J(H,H)=6.8 Hz, 2H, OCH$_2$CH$_2$CH$_2$NH), 1.78 (quintet, $^3$J(H,H)=6.5 Hz, 2H, OCH$_2$CH$_2$CH$_2$NH), 1.59 (bs, 1H, CH$_2$NHCH$_2$), 1.44 (s, 9H, C(CH$_3$)$_3$); $^{13}$C NMR (75 MHz, CDCl$_3$) δ=155.9 (CO), 140.6 (ArCCH$_2$NH), 133.9 (ArCCH$_2$N$_3$), 128.5 (ArCH α to CH$_2$NH), 128.3 (ArCH α to CH$_2$N$_3$), 79.2 (C(CH$_3$)$_3$), 69.7 (OCH$_2$CH$_2$NHBoc), 69.4 (OCH$_2$CH$_2$CH$_2$NH), 54.5 (CH$_2$N$_3$), 53.6 (ArCH$_2$NH), 46.6 (OCH$_2$CH$_2$CH$_2$NH), 40.4 (OCH$_2$CH$_2$NHBoc), 29.9 (OCH$_2$CH$_2$CH$_2$NH), 28.4 (C(CH$_3$)$_3$); HRMS (ESI$^+$): m/z calculated for C$_{18}$H$_{30}$N$_5$O$_3$ [M+H]$^+$: 364.2343, found 364.2354.

1.15 2-Aminoethyl 3-N-(4-(azidomethyl)benzyl)-aminopropyl ether, 16

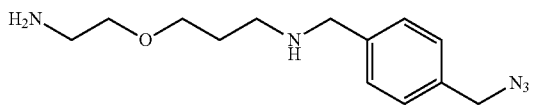

Boc protected amine 15 (360 mg, 0.99 mmol) was dissolved in dry DCM (10 ml) under nitrogen and cooled to 0° C. Trifluoroacetic acid (2 ml) was added and the reaction mixture was stirred for an hour, after which the solvent was evaporated. The residue obtained was dissolved in DCM (30 ml) and NaOH (2 M, 50 ml), the phases were separated and the aqueous phase was extracted with DCM (2×30 ml), dried over Na$_2$SO$_4$, and evaporated yielding 16 as a clear oil (219 mg, 0.83 mmol, 84%). R$_f$=0.40 (9:1 DCM/MeOH saturated with NH$_3$); $^1$H NMR (300 MHz, CDCl$_3$) δ=7.34 (d, $^3$J(H,H)=8.2 Hz, 2H, ArCH α to CH$_2$NH), 7.27 (d, $^3$J(H,H)=8.2 Hz, 2H, ArCH α to CH$_2$N$_3$), 4.32 (s, 2H, CH$_2$N$_3$), 3.80 (s, 2H, CH$_2$NH), 3.53 (t, $^3$J(H,H)=6.2 Hz, 2H, OCH$_2$CH$_2$CH$_2$NH), 3.44 (t, $^3$J(H,H)=5.2 Hz, 2H, OCH$_2$CH$_2$NH$_2$), 2.83 (t, $^3$J(H,H)=5.2 Hz, 2H, OCH$_2$CH$_2$NH$_2$), 2.73 (t, $^3$J(H,H)=6.9 Hz, 2H, OCH$_2$CH$_2$CH$_2$NH), 1.80 (quintet, $^3$J(H,H)=6.5 Hz, 2H, OCH$_2$CH$_2$CH$_2$NH), 1.46 (bs, 3H, NH); $^{13}$C NMR (75 MHz, CDCl$_3$) δ=140.7 (ArCCH$_2$NH), 133.9 (ArCCH$_2$N$_3$), 128.5 (ArCH α to CH$_2$NH), 128.3 (ArCH α to CH$_2$N$_3$), 73.0 (OCH$_2$CH$_2$NH$_2$), 69.5 (OCH$_2$CH$_2$CH$_2$NH), 54.5 (CH$_2$N$_3$), 53.6 (ArCH$_2$NH), 46.8 (OCH$_2$CH$_2$CH$_2$NH), 41.9 (OCH$_2$CH$_2$NH$_2$), 30.0 (OCH$_2$CH$_2$CH$_2$NH); HRMS (ESI$^+$): m/z calculated for C$_{13}$H$_{22}$N$_5$O [M+H]$^+$: 264.1819, found 264.1797.

1.16 2-(pyren-1-ylmethylamino)ethyl 3-N-(4-(azidomethyl)benzyl)-aminopropyl ether, 17

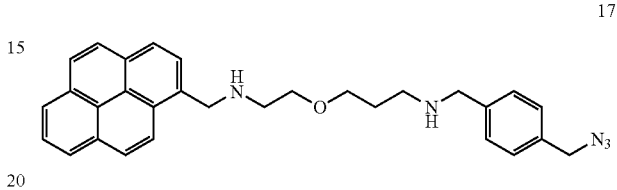

Amine 16 (220 mg, 0.83 mmol) and 1-pyrene carboxaldehyde (230 mg, 1.0 mmol, 1.2 eq) were dissolved in methanol and THF (1:1, 60 ml) and were stirred over night. The reaction mixture was cooled to 0° C. and NaBH$_4$ (157 mg, 4.15 mmol, 5 eq) was added and the solvents was evaporated after stirring for a further hour. The residue obtained was dissolved in DCM (30 ml) and H$_2$O (30 ml), the phases were separated and the aqueous phase was extracted with DCM (2×30 ml), dried over Na$_2$SO$_4$, and evaporated. The crude product was purified by flash chromatography (eluent DCM to DCM/methanol saturated with NH$_3$, 98:2) yielding 17 as a yellow oil (228 mg, 0.48 mmol, 58%). R$_f$=0.80 (9:1 DCM/MeOH saturated with NH$_3$); $^1$H NMR (300 MHz, CDCl$_3$) δ=8.40 (d, $^3$J(H,H)=9.3 Hz, 1H, Pyrene-ArCH), 8.22 (m, 1H, Pyrene-ArCH), 8.20 (m, 1H, Pyrene-ArCH), 8.17 (d, $^3$J(H,H)=7.8 Hz, 1H, Pyrene-ArCH), 8.15 (d, $^3$J(H,H)=9.3 Hz, 1H, Pyrene-ArCH), 8.07 (s, 2H, Pyrene-ArCH), 8.05 (d, $^3$J(H,H)=7.6 Hz, 1H, Pyrene-ArCH), 8.03 (d, $^3$J(H,H)=10.6 Hz, 1H, Pyrene-ArCH), 7.29 (d, $^3$J(H,H)=8.1 Hz, 2H, ArCH α to CH$_2$NH), 7.21 (d, $^3$J(H,H)=8.1 Hz, 2H, ArCH α to CH$_2$N$_3$), 4.52 (s, 2H, CH$_2$Pyrene), 4.26 (s, 2H, CH$_2$N$_3$), 3.73 (s, 2H, CH$_2$NH), 3.64 (t, $^3$J(H,H)=5.2 Hz, 2H, OCH$_2$CH$_2$NH), 3.55 (t, $^3$J(H,H)=6.2 Hz, 2H, OCH$_2$CH$_2$CH$_2$NH), 3.00 (t, $^3$J(H,H)=5.2 Hz, 2H, OCH$_2$CH$_2$NH$_2$), 2.71 (t, $^3$J(H,H)=6.9 Hz, 2H, OCH$_2$CH$_2$CH$_2$NH), 1.82 (quintet, $^3$J(H,H)=6.5 Hz, 2H, OCH$_2$CH$_2$CH$_2$NH), 1.79 (bs, 2H, NH); $^{13}$C NMR (75 MHz, CDCl$_3$) δ=140.4 (ArCCH$_2$NH), 133.7 (ArCCH$_2$N$_3$), 133.6 (Pyrene-ArC), 131.0 (Pyrene-ArC), 130.6 (Pyrene-ArC), 130.4 (Pyrene-ArC), 128.8 (Pyrene-ArC), 128.1 (ArCH α to CH$_2$NH), 128.0 (ArCH α to CH$_2$N$_3$), 127.3 (Pyrene-ArCH), 127.2 (Pyrene-ArCH), 126.8 (Pyrene-ArCH), 126.7 (Pyrene-ArCH), 125.6 (Pyrene-ArCH), 124.8 (Pyrene-ArCH), 124.8 (Pyrene-ArC), 124.7 (Pyrene-ArCH), 124.6 (Pyrene-ArC), 124.4 (Pyrene-ArCH), 123.0 (Pyrene-ArCH), 70.0 (OCH$_2$CH$_2$NH), 69.3 (OCH$_2$CH$_2$CH$_2$NH), 54.2 (CH$_2$N$_3$), 53.3 (ArCH$_2$NH), 51.4 (CH$_2$Pyrene), 49.0 (OCH$_2$CH$_2$NH), 46.5 (OCH$_2$CH$_2$CH$_2$NH), 29.8 (OCH$_2$CH$_2$CH$_2$NH); HRMS (ESI$^+$): m/z calculated for C$_{30}$H$_{32}$N$_5$O [M+H]$^+$: 478.2601, found 478.2570.

1.17 (N-(pyren-1-ylmethyl)-N-(benzyl-2-boronic acid)-aminoethyl) (N'-(4-(azidomethyl)benzyl)-N'-(benzyl-2'-boronic acid)-3-aminopropyl)ether, 18

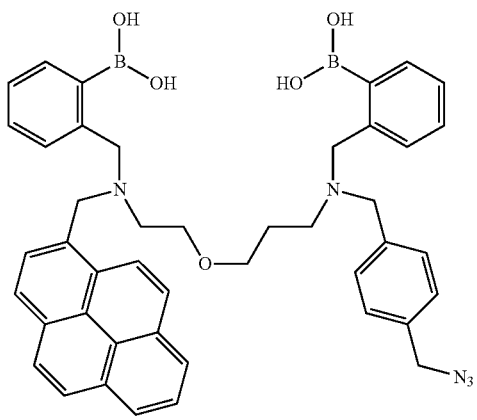

Diamine 17 (228 mg, 0.48 mmol), potassium 2-formylphenyltrifluoroborate (213 mg, 1.00 mmol, 2.1 eq), and sodium triacetoxyborohydride (224 mg, 1.06 mmol, 2.2 eq) were dissolved in dry THF (20 ml) and DIPEA (836 ml, 4.80 mmol, 10 eq) under a nitrogen environment and stirred for 3 days. NaBH$_4$ (36 mg, 0.96 mmol, 2 eq) was added before the solvent was evaporated. The residue obtained was extracted with hot acetone and evaporated before being suspended in acetonitrile/water (10:9) (50 ml). Lithium hydroxide (69 mg, 2.88 mmol, 6 eq) was added and the reaction was stirred at room temperature overnight. The reaction mixture was extracted with ethyl acetate (3×50 ml), the organic phases were combined, dried over magnesium sulphate, and evaporated to yield 18 as a yellow solid (340 mg, 0.46 mmol, 96%). $^1$H NMR (300 MHz, CDCl$_3$/CD$_3$OD 90:10) δ=8.24-7.98 (m, 10H, ArCH), 7.89 (m, ArCH), 7.47-7.31 (m, 6H, ArCH), 7.24 (d, $^3$J(H,H)=8.3 Hz, 2H, ArCH α to CH$_2$N), 7.17 (d, $^3$J(H,H)=8.3 Hz, 2H, ArCH α to CH$_2$N$_3$), 4.33 (s, 2H, CH$_2$Pyrene), 4.22 (s, 2H, CH$_2$N$_3$), 3.98 (s, 2H, (C$_6$H$_4$BOH$_2$CH$_2$N), 3.69 (s, 2H, (C$_6$H$_4$BOH$_2$)CH$_2$N), 3.54 (s, 2H, CH$_2$NH), 3.45 (t, $^3$J(H,H)=5.6 Hz, 2H, OCH$_2$CH$_2$N), 3.23 (t, $^3$J(H,H)=6.1 Hz, 2H, OCH$_2$CH$_2$CH$_2$N), 2.79 (t, $^3$J(H,H)=5.6 Hz, 2H, OCH$_2$CH$_2$N), 2.51 (m, 2H, OCH$_2$CH$_2$CH$_2$NH), 1.76 (m, 2H, OCH$_2$CH$_2$CH$_2$NH); $^{11}$B NMR (96 MHz, CDCl$_3$/CD$_3$OD 95:5) δ=-9.4 $^{13}$C NMR (75 MHz, CDCl$_3$/CD$_3$OD 90:10) δ=143.8 (ArCH), 141.5 (ArC), 141.1 (ArC), 136.4 (ArCCH$_2$N), 135.8 (ArCH), 135.7 (ArCH), 134.3 (ArCCH$_2$N$_3$), 131.1 (ArCH), 131.1 (ArC), 130.7 (ArC), 130.6 (ArCH), 130.5 (ArC), 130.3 (ArC), 129.8 (ArCH), 129.7 (ArC), 129.7 (ArCH α to CH$_2$N), 128.6 (ArCH), 128.0 (ArCH α to CH$_2$N$_3$), 127.3 (ArCH), 127.3 (ArCH), 127.3 (ArCH), 127.2 (ArCH), 127.1 (ArCH), 125.8 (ArCH), 125.1 (ArCH), 124.9 (ArCH), 124.7 (ArC), 124.5 (ArC), 124.4 (ArCH), 123.1 (ArCH), 68.7 (OCH$_2$CH$_2$CH$_2$N), 67.9 (OCH$_2$CH$_2$N), 62.4 ((C$_6$H$_4$BOH$_2$)CH$_2$N), 61.0 ((C$_6$H$_4$BOH$_2$)CH$_2$N), 56.6 (ArCH$_2$N), 54.8 (CH$_2$Pyrene), 54.1 (CH$_2$N$_3$), 53.3 (ArCH$_2$N), 52.0 (OCH$_2$CH$_2$N), 49.2 (OCH$_2$CH$_2$CH$_2$N), 25.0 (OCH$_2$CH$_2$CH$_2$N); HRMS (ESI$^+$): m/z calculated for C$_{44}$H$_{44}$B$_2$N$_5$O$_4$ [M+H−H$_2$O]$^+$: 728.3574, found 728.3525.

Example 2

Binding Studies

Fluorescence titration studies were carried out with glucose sensor molecule 18 synthesised as described in Example 1 above, as well as with two comparative compounds 19 and 20:

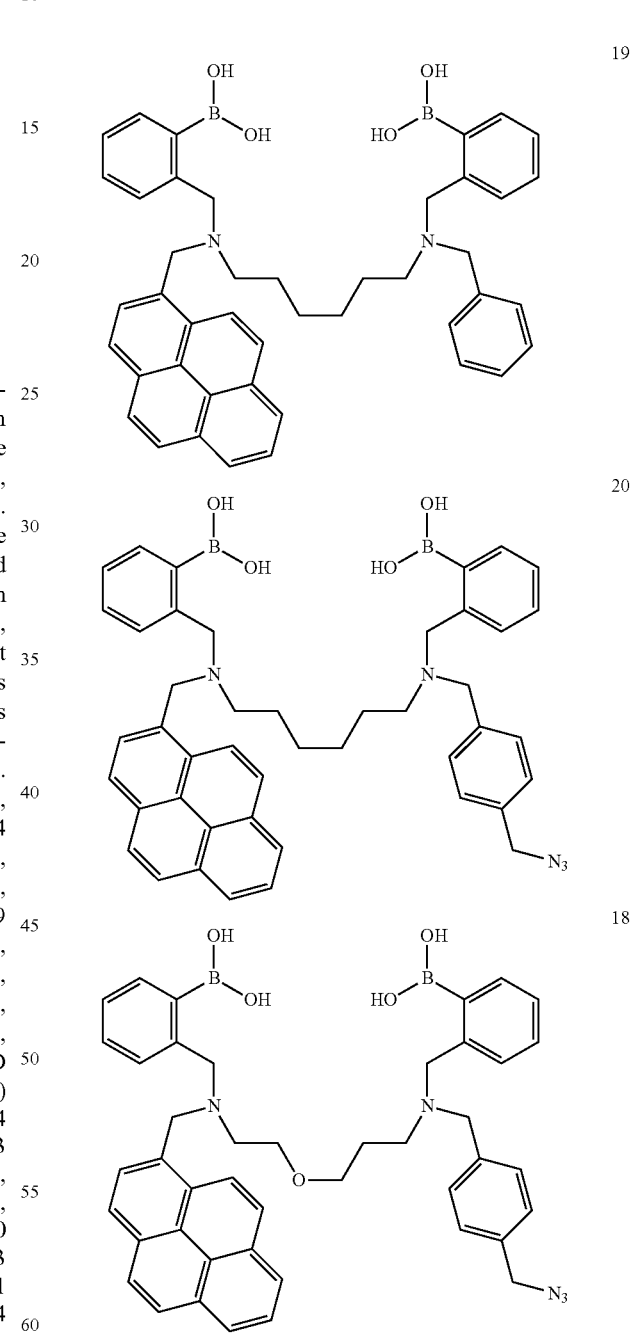

Compound 19 was synthesised according to the procedure of Arimori, S.; Bell, M. L.; Oh, C. S.; Frimat, K. A.; James, T. D. *Chem. Commun.* 2001, 1836. Compound 20 was synthesised in a similar manner, with appropriate modification at position R$_4$.

For each sensor compound, titrations were carried out using D-glucose, D-fructose, D-mannose and D-galactose, according to the following standard procedure:

Stock solutions of carbohydrates were made up in an aqueous methanolic buffer [52.1 wt % methanol, KCl (10.0 mM), $KH_2PO_4$ (2.75 mM) and $Na_2HPO_4$ (2.75 mM)] at a pH of 8.21 and allowed to equilibrate overnight prior to use. Additions to receptor were performed using a procedure which kept [host] (i.e. [receptor]) and the total volume constant while raising [guest] (i.e. [carbohydrate]). Thus, receptor was added to a stock carbohydrate solution to give [host]=0.1 or 1.0 μM. This solution was used as titrant. A solution of guest in an aqueous methanolic buffer [52.1 wt % methanol, KCl (10.0 mM), $KH_2PO_4$ (2.75 mM) and $Na_2HPO_4$ (2.75 mM)] at a pH of 8.21, also 0.1 or 1.0 μM, was placed in a fluorescence cell. For each addition, an aliquot of a certain volume was removed from the cell, and the same volume of titrant was then added. The mixture was shaken then sonicated, and the fluorescence spectrum recorded on a PerkinElmer LS 50B fluorescence spectrometer at room temperature. The excitation wavelength was set at 342 nm. Emission changes in counts per second (DCPS) were analysed according to a 1:1 binding model, using a non-linear least squares curve-fitting program implemented within Excel for calculation of a association constant $K_{obs}$. In the case of D-fructose, an attempt to analyse the data according to the 1:1 binding model yielded a very poor fit. Instead, the intensity changes were analysed according to a 1:1+1:2 binding model, using the program WinEqNMR.

Results:

TABLE 1

Observed 1:1 stability constants ($K_{obs}$), determination coefficient ($r^2$), and fluorescence enhancement for receptors 18-20 (0.1 μM) with D-glucose, D-fructose, D-galactose, and D-mannose.

| | 19 | | 20 | | 18 | |
|---|---|---|---|---|---|---|
| | $K_{obs}/M^{-1}$ | $I_\infty/I_0$ | $K_{obs}/M^{-1}$ | $I_\infty/I_0$ | $K_{obs}/M^{-1}$ | $I_\infty/I_0$ |
| D-Glucose | 962 ± 70 | 2.8 | 1072 ± 185 | 4.6 | 1476 ± 51 | 4.4 |
| D-Galactose | 657 ± 39 | 3.1 | 536 ± 42 | 1.8 | 243 ± 16 | 2.8 |
| D-Fructose | 784 ± 44 | 3.2 | 3542 ± 500 | 1.0 | $K_{obs1}$ = 765 ± 260; $K_{obs2}$ = 210 ± 1553 | 1.5 |
| D-Mannose | 74 ± 3 | 2.8 | 101 ± 8 | 2.0 | 48 ± 4 | 2.5 |

Figure 2:
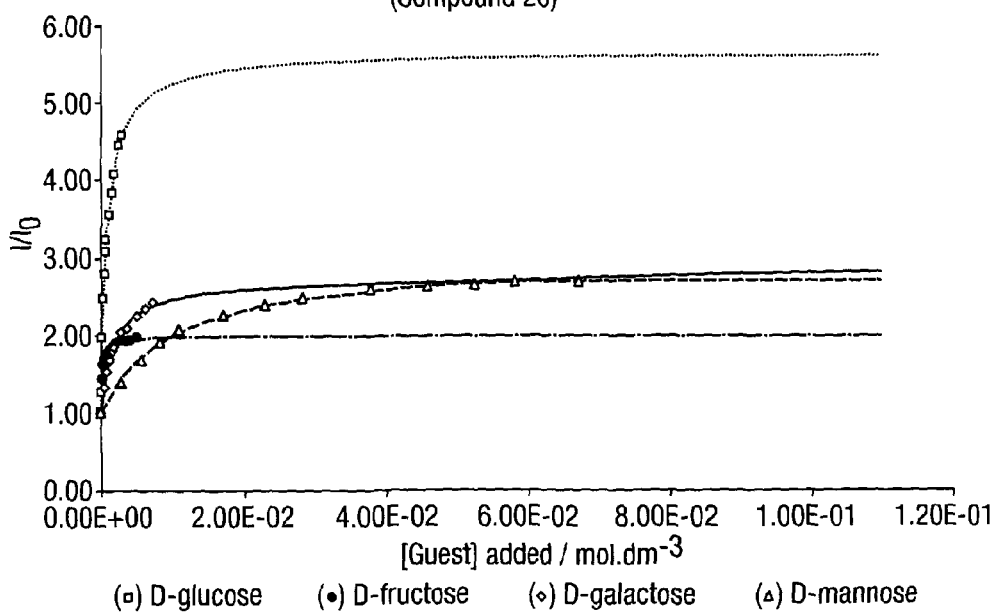

The results are also depicted graphically in FIGS. 1 to 3. FIG. 1 shows the relative fluorescence intensity versus carbohydrate concentration profile of 18 (0.1 μM, $\lambda_{ex}$=342 nm, $\lambda_{em}$≈377 nm) displaying photoinduced electron transfer (PET) with (■) D-glucose, (●) D-fructose, (♦) D-galactose, (▲) D-mannose. FIG. 2 provides corresponding results for compound 20. FIG. 3 shows the relative fluorescence intensity versus carbohydrate concentration profile of 19 from literature data.

The results show that the glucose sensor molecule of the invention has greater affinity and selectivity for D-glucose than compounds 19 and 20, which do not contain an oxygen atom in the carbon chain in the glucose binding site.

Example 3

Attachment of Glucose Sensor Molecule to Hydrogel

A solution of AIPD (8 mg) in $H_2O$ (700 μl) was added to a solution of compound 21 (16 mg), dimethylacrylamide (740 mg) and PEG-DMA 600 (1.40 ml) in a aqueous TFA solution (5 mM, 700 μl) under nitrogen. This solution was then heated for 1 hour at 45° C. followed by 1.5 hours at 60° C. to yield a boronic acid receptor containing hydrogel. The polymerisation was then quenched by submerging the reaction vessel in ice water.

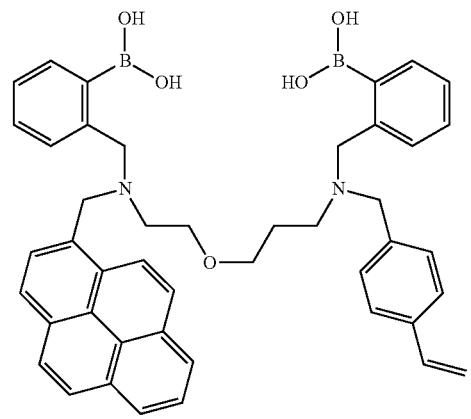

21

The invention claimed is:

1. A glucose sensor comprising a glucose receptor having a binding site of formula (I):

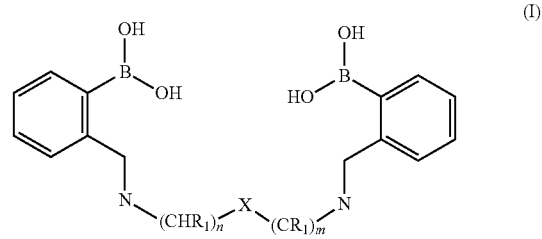

(I)

wherein X represents O or S;

n is from 1 to 4;

m is from 1 to 4, and n+m is 5;

each $R_1$ is the same or different and represents hydrogen, $C_{1-4}$ alkyl or $C_{3-7}$ cycloalkyl;

or $R_1$, together with an adjacent $R_1$ group and the carbon or nitrogen atoms to which they are attached, form a $C_{3-7}$ cycloalkyl or a 5- or 6-membered heterocyclyl group.

2. A glucose sensor according to claim 1, wherein X represents O.

3. A glucose sensor according to claim 1, wherein each $R_1$ is the same or different and represents hydrogen, $C_{1-4}$ alkyl or $C_{3-7}$ cycloalkyl; and $R_2$ represents hydrogen or $C_{1-4}$ alkyl.

4. A glucose sensor according to claim 1, wherein at least four $R_1$ groups represent hydrogen.

5. A glucose sensor according to claim 1, wherein
X represents O;
n is from 1 to 4;
m is from 1 to 4 and n+m is 5; and
each $R_1$ represents hydrogen.

6. A glucose sensor according to claim 5, wherein n is 2 or 3, m is 2 or 3 and n+m is 5.

7. A glucose sensor according to claim 1, wherein the glucose receptor is bonded to a support material at one of the nitrogen atoms marked as N*:

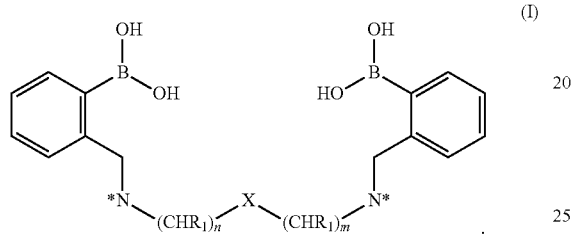
(I)

8. A glucose sensor according to claim 7, wherein the support material is a dendrimer or water-soluble polymer and the resulting complex of receptor and support material is in aqueous solution.

9. A glucose sensor according to claim 1, wherein the sensor further comprises a fluorophore, the fluorophore being associated with the glucose receptor such that when glucose is bound to the receptor, the fluorescence of the fluorophore is perturbed.

10. A glucose sensor according to claim 1, wherein the sensor comprises a glucose sensor molecule of formula (II):

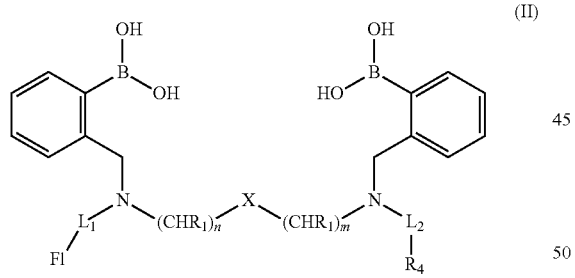
(II)

wherein X, n, m and $R_1$ are as defined in claim 1;
Fl is a fluorophore;
$L_1$ and $L_2$ are the same or different and represent a linker; and
$R_4$ is a support material or a hydrogen atom.

11. A glucose sensor according to claim 10, wherein $L_1$ and $L_2$ are the same or different and each consists of one or more $C_{1-6}$ alkylene groups and/or one or more arylene groups.

12. A glucose sensor according to claim 11, wherein $L_2$ is a group of formula —$(CH_2)_s$-Ph-$(CH_2)_t$—, wherein s is 1 or 2, t is 0, 1 or 2 and Ph is phenylene; and/or $L_1$ is methylene or ethylene.

13. A glucose sensor according to claim 10, wherein the sensor comprises a glucose sensor molecule of formula (II') or (II"):

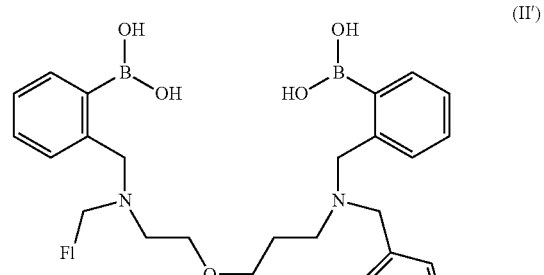
(II')

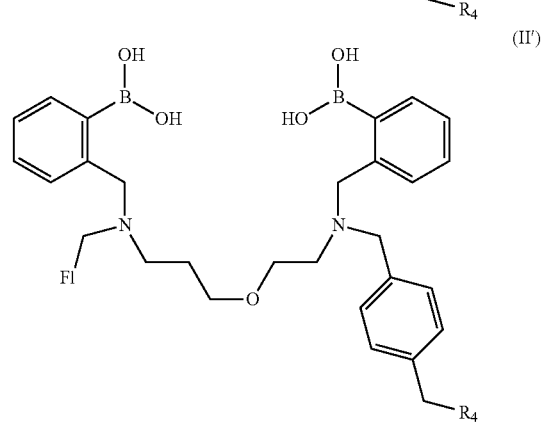
(II")

wherein
Fl is a fluorophore; and
$R_4$ is a support material or a hydrogen atom.

14. A glucose sensor according to claim 10, wherein $R_4$ is a support material and the support material is a polymeric matrix, a water-soluble polymer or a water soluble molecule selected from dendrimers, cyclodextrins, cryptans and crown ethers.

15. A glucose sensor molecule of formula (II):

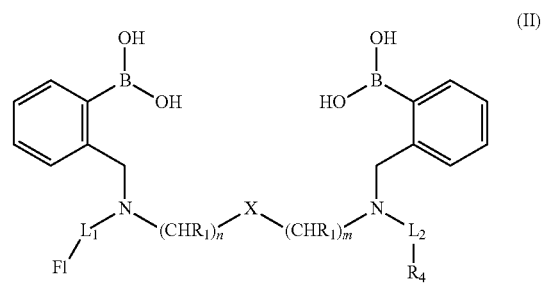
(II)

wherein X, n, m and $R_1$ are as defined in claim 1;
Fl is a fluorophore;
$L_1$ and $L_2$ are the same or different and represent a linker; and
$R_4$ is a support material, a hydrogen atom or an anchor group suitable for attaching the sensor molecule to a support material, wherein the support material is selected from the group consisting of a polymeric matrix, a water-soluble polymer or a water soluble molecule selected from dendrimers, cyclodextrins, cryptans, and crown ethers.

16. A glucose sensor molecule according to claim 15, wherein $R_4$ is an anchor group selected from an alkene, ester, aldehyde, amine or azide group.

17. A process for the preparation of a glucose sensor molecule as claimed in claim 15, which process comprises reductive amination of (III) in the presence of (IV), followed by deprotection of the boronic acid group:

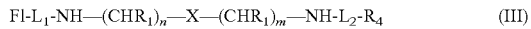

$$Fl\text{-}L_1\text{-}NH\text{—}(CHR_1)_n\text{—}X\text{—}(CHR_1)_m\text{—}NH\text{-}L_2\text{-}R_4 \qquad (III)$$

wherein X, n, m and $R_1$ are as defined in claim 1;
Fl is a fluorophore;
$L_1$ and $L_2$ are the same or different and represent a linker; and
$R_4$ is a hydrogen atom or an anchor group suitable for attaching the sensor molecule to a support material;

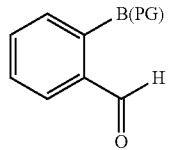

wherein B(PG) is a boronic acid group protected by a protecting group.

18. A method of detecting or quantifying the amount of glucose in an analyte, the method comprising contacting the analyte with a glucose receptor comprising a binding site of formula (I):

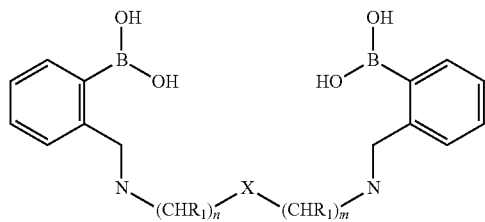

wherein X, n, m and $R_1$ are as defined in claim 1.

19. A method according to claim 18, which method is a fluorescence sensing method comprising detecting a change in the fluorescence of the sensor when glucose is bound to the glucose receptor.

20. A method according to claim 19, wherein the change in fluorescence is a change in fluorescence lifetime.

21. A process according to claim 17, wherein the change in fluorescence is a change in fluorescence intensity.

22. A process for the preparation of a glucose sensor molecule as claimed in claim 15, which process comprises reductive amination of (III) in the presence of (IV), followed by deprotection of the boronic acid group and deprotection of $R_4$:

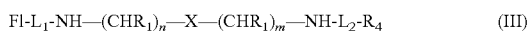

$$Fl\text{-}L_1\text{-}NH\text{—}(CHR_1)_n\text{—}X\text{—}(CHR_1)_m\text{—}NH\text{-}L_2\text{-}R_4 \qquad (III)$$

wherein X, n, m and $R_1$ are as defined in claim 1;
Fl is a fluorophore;
$L_1$ and $L_2$ are the same or different and represent a linker; and
$R_4$ is a hydrogen atom or an anchor group suitable for attaching the sensor molecule to a support material, wherein $R_4$ is protected by a protecting group;

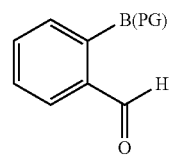

wherein B(PG) is a boronic acid group protected by a protecting group.

23. A glucose sensor molecule according to claim 15 wherein $L_1$ and $L_2$ are the same or different and each consists of one or more $C_{1-6}$ alkylene groups and/or one or more arylene groups.

24. A glucose sensor molecule according to claim 15, wherein $L_2$ is a group of formula $—(CH_2)_s\text{-}Ph\text{-}(CH_2)_t—$, wherein s is 1 or 2, t is 0, 1 or 2 and Ph is phenylene; and/or $L_1$ is methylene or ethylene.

* * * * *